(12) United States Patent
Armstrong et al.

(10) Patent No.: US 9,956,389 B2
(45) Date of Patent: May 1, 2018

(54) APPARATUSES AND METHODS FOR NEGATIVE PRESSURE WOUND THERAPY

(71) Applicant: Smith & Nephew Inc., Memphis, TN (US)

(72) Inventors: Ed Armstrong, Palm Harbor, FL (US); Iain Michael Blackburn, East Yorkshire (GB); Robert Emmerson, East Riding of Yorkshire (GB); Michael B. Mosholder, Palm Harbor, FL (US)

(73) Assignee: Smith & Nephew, Inc., Memphis, TN (US)

( * ) Notice: Subject to any disclaimer, the term of this patent is extended or adjusted under 35 U.S.C. 154(b) by 242 days.

(21) Appl. No.: 14/730,040

(22) Filed: Jun. 3, 2015

(65) Prior Publication Data

US 2015/0343194 A1 Dec. 3, 2015

Related U.S. Application Data

(63) Continuation of application No. 13/381,884, filed as application No. PCT/US2011/041521 on Jun. 22, 2011, now Pat. No. 9,050,398.

(Continued)

(51) Int. Cl.
*A61M 27/00* (2006.01)
*A61M 39/10* (2006.01)
(Continued)

(52) U.S. Cl.
CPC ... *A61M 39/1011* (2013.01); *A61F 13/00068* (2013.01); *A61M 1/0023* (2013.01);
(Continued)

(58) Field of Classification Search
CPC combination set(s) only.
See application file for complete search history.

(56) References Cited

U.S. PATENT DOCUMENTS

| 1,585,104 A | 5/1926 | Montgomery |
| 2,736,317 A | 2/1956 | Alexander |

(Continued)

FOREIGN PATENT DOCUMENTS

| AU | 674837 B2 | 1/1997 |
| DE | 3 907 007 | 9/1990 |

(Continued)

OTHER PUBLICATIONS

US 7,186,244, 03/2007, Hunt et al. (withdrawn)

(Continued)

*Primary Examiner* — Tatyana Zalukaeva
*Assistant Examiner* — Guy K Townsend
(74) *Attorney, Agent, or Firm* — Knobbe, Martens, Olson & Bear LLP

(57) ABSTRACT

Disclosed herein are several embodiments of a reduced pressure appliance and methods of using the same in the treatment of wounds. Some embodiments are directed to improved fluidic connectors or suction adapters for connecting to a wound site, for example using softer, kink-free conformable suction adapters. Certain embodiments are directed to connectors used to connect fluid passage tube used in transmitting negative pressure to a fabric channel used in a suction adapter.

17 Claims, 19 Drawing Sheets

Related U.S. Application Data

(60) Provisional application No. 61/426,432, filed on Dec. 22, 2010.

(51) Int. Cl.
*A61F 13/00* (2006.01)
*F16L 21/00* (2006.01)
*F16L 37/08* (2006.01)
*A61M 1/00* (2006.01)

(52) U.S. Cl.
CPC ........ *A61M 1/0052* (2014.02); *A61M 1/0086* (2014.02); *A61M 1/0088* (2013.01); *A61M 1/0092* (2014.02); *A61M 39/10* (2013.01); *F16L 21/00* (2013.01); *F16L 37/08* (2013.01); *A61M 2039/1027* (2013.01); *A61M 2205/7518* (2013.01); *A61M 2205/7563* (2013.01); *A61M 2210/04* (2013.01)

(56) References Cited

U.S. PATENT DOCUMENTS

| | | | |
|---|---|---|---|
| 3,042,041 A | 7/1962 | Jascalevich | |
| 3,255,749 A * | 6/1966 | Smithers | A61F 13/0273 128/DIG. 15 |
| 3,568,675 A | 3/1971 | Harvey | |
| 3,572,340 A | 3/1971 | Lloyd et al. | |
| 3,874,387 A | 4/1975 | Barbieri | |
| 3,880,164 A | 4/1975 | Stepno | |
| 3,927,443 A * | 12/1975 | Brumlik | A44B 18/0015 24/442 |
| 4,080,970 A | 3/1978 | Miller | |
| 4,164,027 A | 8/1979 | Bonnie et al. | |
| 4,169,303 A * | 10/1979 | Lemelson | A44B 18/0061 24/446 |
| 4,231,357 A | 11/1980 | Hessner | |
| 4,261,363 A | 4/1981 | Russo | |
| 4,360,015 A | 11/1982 | Mayer | |
| 4,382,441 A | 5/1983 | Svedman | |
| 4,392,853 A | 7/1983 | Muto | |
| 4,468,219 A | 8/1984 | George et al. | |
| 4,540,412 A | 9/1985 | Van Overloop | |
| 4,553,967 A | 11/1985 | Ferguson et al. | |
| 4,561,435 A | 12/1985 | McKnight et al. | |
| 4,569,674 A | 2/1986 | Phillips | |
| 4,579,120 A | 4/1986 | MacGregor | |
| 4,605,399 A | 8/1986 | Weston et al. | |
| 4,614,183 A | 9/1986 | McCracken et al. | |
| 4,665,909 A * | 5/1987 | Trainor | A61F 13/0273 602/75 |
| 4,906,240 A | 3/1990 | Reed et al. | |
| 4,921,492 A | 5/1990 | Schultz | |
| 4,941,882 A | 7/1990 | Ward et al. | |
| 4,969,880 A | 11/1990 | Zamierowski | |
| 4,980,226 A | 12/1990 | Hellgren et al. | |
| 5,009,224 A | 4/1991 | Cole | |
| 5,056,510 A | 10/1991 | Gilman | |
| 5,060,642 A | 10/1991 | Gilman | |
| 5,088,483 A | 2/1992 | Heinecke | |
| 5,100,396 A | 3/1992 | Zamierowski | |
| 5,106,362 A | 4/1992 | Gilman | |
| 5,112,323 A | 5/1992 | Winkler et al. | |
| 5,134,007 A | 7/1992 | Reising et al. | |
| 5,147,698 A | 9/1992 | Cole | |
| 5,149,331 A | 9/1992 | Ferdman et al. | |
| 5,152,757 A | 10/1992 | Eriksson | |
| 5,160,315 A | 11/1992 | Heinecke et al. | |
| 5,160,334 A | 11/1992 | Billings et al. | |
| 5,176,663 A | 1/1993 | Svedman et al. | |
| 5,180,375 A | 1/1993 | Feibus | |
| 5,218,973 A * | 6/1993 | Weaver | A61B 5/0408 607/152 |
| 5,230,496 A | 7/1993 | Shillington et al. | |
| 5,244,457 A | 9/1993 | Karami et al. | |
| 5,261,893 A | 11/1993 | Zamierowski | |
| 5,263,922 A | 11/1993 | Soya et al. | |
| 5,300,054 A | 4/1994 | Feist et al. | |
| 5,304,161 A | 4/1994 | Noel et al. | |
| 5,308,313 A | 5/1994 | Karami et al. | |
| 5,366,451 A | 11/1994 | Levesque | |
| 5,391,161 A | 2/1995 | Hellgren et al. | |
| 5,437,651 A | 8/1995 | Todd et al. | |
| 5,439,458 A | 8/1995 | Noel et al. | |
| 5,447,492 A | 9/1995 | Cartmell et al. | |
| 5,486,167 A | 1/1996 | Dragoo et al. | |
| 5,520,629 A | 5/1996 | Heinecke et al. | |
| 5,525,407 A | 6/1996 | Yang | |
| 5,527,293 A * | 6/1996 | Zamierowski | A61F 5/453 128/898 |
| 5,527,923 A | 6/1996 | Klingler et al. | |
| 5,531,855 A | 7/1996 | Heinecke et al. | |
| 5,549,584 A | 8/1996 | Gross | |
| 5,593,750 A | 1/1997 | Rothrum et al. | |
| 5,599,289 A | 2/1997 | Castellana | |
| 5,603,145 A | 2/1997 | Arakawa et al. | |
| 5,613,942 A | 3/1997 | Lucast et al. | |
| 5,618,278 A | 4/1997 | Rothrum | |
| 5,624,423 A | 4/1997 | Anjur et al. | |
| 5,636,643 A | 6/1997 | Argenta et al. | |
| 5,637,093 A | 6/1997 | Hyman et al. | |
| 5,645,081 A | 7/1997 | Argenta et al. | |
| 5,678,564 A | 10/1997 | Lawrence et al. | |
| 5,695,846 A | 12/1997 | Lange et al. | |
| 5,701,917 A | 12/1997 | Khouri | |
| 5,738,642 A | 4/1998 | Heinecke et al. | |
| 5,795,584 A | 8/1998 | Totakura et al. | |
| 5,797,844 A | 8/1998 | Yoshioka et al. | |
| 5,797,894 A | 8/1998 | Cadieux et al. | |
| 5,894,608 A | 4/1999 | Birbara | |
| 5,910,150 A * | 6/1999 | Saadat | A61B 17/3207 604/22 |
| 5,911,222 A | 6/1999 | Lawrence et al. | |
| 5,914,282 A | 6/1999 | Dunshee et al. | |
| 5,964,723 A | 10/1999 | Augustine | |
| 6,071,267 A * | 6/2000 | Zamierowski | A61F 13/0203 604/289 |
| 6,117,111 A | 9/2000 | Fleischmann | |
| 6,121,508 A | 9/2000 | Bischof et al. | |
| 6,142,982 A | 11/2000 | Hunt et al. | |
| 6,169,224 B1 | 1/2001 | Heinecke et al. | |
| 6,264,976 B1 | 7/2001 | Heinecke et al. | |
| 6,291,050 B1 | 9/2001 | Cree et al. | |
| 6,345,623 B1 | 2/2002 | Heaton et al. | |
| 6,406,447 B1 | 6/2002 | Thrash et al. | |
| 6,420,622 B1 | 7/2002 | Johnston et al. | |
| 6,436,432 B2 | 8/2002 | Heinecke et al. | |
| 6,458,109 B1 | 10/2002 | Henley et al. | |
| 6,461,467 B2 | 10/2002 | Blatchford et al. | |
| 6,479,073 B1 | 11/2002 | Lucast et al. | |
| 6,553,998 B2 | 4/2003 | Heaton et al. | |
| 6,566,575 B1 | 5/2003 | Stickels et al. | |
| 6,607,799 B1 | 8/2003 | Heinecke et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,685,682 B1 | 2/2004 | Heinecke et al. | |
| 6,752,794 B2 | 6/2004 | Lockwood et al. | |
| 6,755,807 B2 | 6/2004 | Risk et al. | |
| 6,814,079 B2 | 11/2004 | Heaton et al. | |
| 6,838,589 B2 | 1/2005 | Liedtke et al. | |
| 6,855,135 B2 | 2/2005 | Lockwood et al. | |
| 6,867,342 B2 | 3/2005 | Johnston et al. | |
| 6,878,857 B1 | 4/2005 | Chihani et al. | |
| 6,903,243 B1 | 6/2005 | Burton | |
| 6,936,037 B2 | 8/2005 | Bubb | |
| 6,951,553 B2 | 10/2005 | Bubb et al. | |
| D515,701 S | 2/2006 | Horhota et al. | |
| 6,994,702 B1 | 2/2006 | Johnson | |
| 6,994,904 B2 | 2/2006 | Joseph et al. | |
| 7,004,915 B2 | 2/2006 | Boynton et al. | |
| 7,005,143 B2 | 2/2006 | Abuelyaman et al. | |
| 7,048,818 B2 * | 5/2006 | Krantz | A44B 18/0049 156/244.25 |

(56) References Cited

U.S. PATENT DOCUMENTS

| | | | |
|---|---|---|---|
| 7,070,580 B2 | 7/2006 | Nielsen | |
| 7,070,584 B2 | 7/2006 | Johnson et al. | |
| 7,108,683 B2* | 9/2006 | Zamierowski | A61M 1/0058 |
| | | | 604/304 |
| 7,117,869 B2 | 10/2006 | Heaton et al. | |
| 7,128,735 B2 | 10/2006 | Weston | |
| 7,183,454 B1 | 2/2007 | Rosenberg | |
| 7,195,624 B2 | 3/2007 | Lockwood | |
| 7,198,046 B1 | 4/2007 | Argenta et al. | |
| 7,216,651 B2 | 5/2007 | Argenta et al. | |
| 7,273,054 B2 | 9/2007 | Heaton et al. | |
| 7,276,247 B2 | 10/2007 | Fansler et al. | |
| 7,279,612 B1 | 10/2007 | Heaton et al. | |
| 7,285,576 B2 | 10/2007 | Hyde et al. | |
| 7,316,672 B1 | 1/2008 | Hunt et al. | |
| 7,338,482 B2 | 3/2008 | Lockwood et al. | |
| 7,381,859 B2 | 6/2008 | Hunt et al. | |
| 7,438,705 B2 | 10/2008 | Karpowicz et al. | |
| 7,442,849 B2 | 10/2008 | Heinecke | |
| 7,485,112 B2 | 2/2009 | Karpowicz et al. | |
| 7,503,910 B2 | 3/2009 | Adahan | |
| 7,531,711 B2 | 5/2009 | Sigurjonsson et al. | |
| 7,534,927 B2 | 5/2009 | Lockwood | |
| 7,569,742 B2 | 8/2009 | Haggstrom et al. | |
| 7,585,554 B2 | 9/2009 | Johnson et al. | |
| 7,586,019 B2 | 9/2009 | Oelund et al. | |
| 7,615,036 B2 | 11/2009 | Joshi et al. | |
| 7,625,362 B2 | 12/2009 | Boehringer et al. | |
| 7,645,269 B2 | 1/2010 | Zamierowski | |
| 7,651,484 B2 | 1/2010 | Heaton et al. | |
| 7,670,323 B2 | 3/2010 | Hunt et al. | |
| 7,678,102 B1 | 3/2010 | Heaton | |
| 7,686,785 B2 | 3/2010 | Boehringer et al. | |
| 7,723,560 B2* | 5/2010 | Lockwood | A61M 1/0084 |
| | | | 602/41 |
| 7,745,681 B1 | 6/2010 | Ferguson | |
| 7,754,937 B2 | 7/2010 | Boehringer et al. | |
| 7,758,554 B2 | 7/2010 | Lina et al. | |
| 7,759,537 B2 | 7/2010 | Bishop et al. | |
| 7,759,539 B2 | 7/2010 | Shaw et al. | |
| 7,776,028 B2 | 8/2010 | Miller et al. | |
| 7,779,625 B2 | 8/2010 | Joshi et al. | |
| 7,781,639 B2 | 8/2010 | Johnston et al. | |
| 7,794,438 B2 | 9/2010 | Henley et al. | |
| 7,794,450 B2* | 9/2010 | Blott | A61M 35/00 |
| | | | 128/897 |
| 7,815,616 B2 | 10/2010 | Boehringer et al. | |
| 7,846,141 B2 | 12/2010 | Weston | |
| 7,862,718 B2 | 1/2011 | Doyen et al. | |
| 7,880,050 B2 | 2/2011 | Robinson et al. | |
| 7,896,856 B2 | 3/2011 | Petrosenko et al. | |
| 7,896,864 B2 | 3/2011 | Lockwood et al. | |
| 7,922,703 B2 | 4/2011 | Riesinger | |
| 7,942,866 B2* | 5/2011 | Radl | A61M 1/0011 |
| | | | 604/317 |
| 7,951,124 B2 | 5/2011 | Boehringer et al. | |
| 7,976,533 B2 | 7/2011 | Larsson | |
| 7,981,098 B2 | 7/2011 | Boehringer et al. | |
| 8,002,313 B2 | 8/2011 | Singh et al. | |
| 8,007,257 B2 | 8/2011 | Heaton et al. | |
| 8,021,347 B2 | 9/2011 | Vitaris et al. | |
| 8,057,449 B2 | 11/2011 | Sanders et al. | |
| 8,083,712 B2 | 12/2011 | Biggie et al. | |
| 8,100,887 B2 | 1/2012 | Weston et al. | |
| 8,114,126 B2 | 2/2012 | Heaton et al. | |
| 8,133,211 B2 | 3/2012 | Cavanaugh, II et al. | |
| 8,142,419 B2 | 3/2012 | Heaton et al. | |
| 8,147,468 B2 | 4/2012 | Barta et al. | |
| 8,148,595 B2 | 4/2012 | Robinson et al. | |
| 8,148,596 B2 | 4/2012 | Miau et al. | |
| 8,152,785 B2 | 4/2012 | Vitaris | |
| 8,158,844 B2 | 4/2012 | McNeil | |
| 8,162,907 B2 | 4/2012 | Heagle | |
| 8,168,848 B2 | 5/2012 | Lockwood et al. | |
| 8,188,331 B2 | 5/2012 | Barta et al. | |
| 8,192,409 B2 | 6/2012 | Hardman et al. | |
| 8,197,467 B2 | 6/2012 | Heaton et al. | |
| 8,202,261 B2 | 6/2012 | Kazala, Jr. et al. | |
| 8,235,939 B2 | 8/2012 | Johnson et al. | |
| 8,241,261 B2 | 8/2012 | Randolph et al. | |
| 8,298,200 B2 | 10/2012 | Vess et al. | |
| 8,382,731 B2 | 2/2013 | Johannison | |
| D679,819 S | 4/2013 | Peron | |
| D679,820 S | 4/2013 | Peron | |
| 8,608,776 B2 | 12/2013 | Coward et al. | |
| 8,623,047 B2* | 1/2014 | Cornet | A61B 17/085 |
| | | | 604/543 |
| 8,708,998 B2 | 4/2014 | Weston et al. | |
| 8,721,629 B2* | 5/2014 | Hardman | A61B 17/085 |
| | | | 604/543 |
| 8,734,410 B2 | 5/2014 | Hall et al. | |
| 8,771,244 B2 | 7/2014 | Eckstein et al. | |
| 8,784,392 B2 | 7/2014 | Vess et al. | |
| 8,801,685 B2 | 8/2014 | Armstrong et al. | |
| 8,814,842 B2 | 8/2014 | Coulthard et al. | |
| D714,433 S | 9/2014 | Armstrong et al. | |
| 8,843,327 B2 | 9/2014 | Vernon-Harcourt et al. | |
| 8,905,985 B2 | 12/2014 | Allen et al. | |
| 8,951,235 B2 | 2/2015 | Allen et al. | |
| 9,017,302 B2 | 4/2015 | Vitaris et al. | |
| 9,050,398 B2 | 6/2015 | Armstrong et al. | |
| 9,061,095 B2 | 6/2015 | Adie et al. | |
| D746,435 S | 12/2015 | Armstrong et al. | |
| RE45,864 E | 1/2016 | Peron | |
| 9,227,000 B2 | 1/2016 | Fink et al. | |
| 9,327,065 B2 | 5/2016 | Alberti et al. | |
| 9,474,654 B2 | 10/2016 | Heagle et al. | |
| RE46,289 E | 1/2017 | Peron | |
| 9,681,993 B2 | 6/2017 | Wu et al. | |
| 2001/0034223 A1 | 10/2001 | Rieser et al. | |
| 2002/0002209 A1 | 1/2002 | Mork | |
| 2002/0182246 A1 | 12/2002 | Oyaski | |
| 2003/0050594 A1 | 3/2003 | Zamierowski | |
| 2004/0039415 A1 | 2/2004 | Zamierowski | |
| 2004/0054338 A1* | 3/2004 | Bybordi | A61M 1/0088 |
| | | | 604/313 |
| 2004/0064132 A1 | 4/2004 | Boehringer et al. | |
| 2005/0004534 A1* | 1/2005 | Lockwood | A61M 1/0031 |
| | | | 604/304 |
| 2005/0020955 A1 | 1/2005 | Sanders et al. | |
| 2005/0065484 A1 | 3/2005 | Watson, Jr. | |
| 2005/0085795 A1 | 4/2005 | Lockwood | |
| 2005/0101940 A1 | 5/2005 | Radl et al. | |
| 2005/0137539 A1 | 6/2005 | Biggie et al. | |
| 2005/0273066 A1 | 12/2005 | Wittmann | |
| 2006/0009744 A1 | 1/2006 | Erdman et al. | |
| 2006/0036221 A1 | 2/2006 | Watson, Jr. | |
| 2006/0079852 A1 | 4/2006 | Bubb et al. | |
| 2006/0100586 A1 | 5/2006 | Karpowicz | |
| 2007/0038172 A1 | 2/2007 | Zamierowski | |
| 2007/0129707 A1* | 6/2007 | Blott | A61M 1/0058 |
| | | | 604/543 |
| 2007/0156104 A1 | 7/2007 | Lockwood et al. | |
| 2007/0167927 A1 | 7/2007 | Hunt et al. | |
| 2007/0219497 A1 | 9/2007 | Johnson et al. | |
| 2007/0219512 A1* | 9/2007 | Heaton | A61M 1/0088 |
| | | | 604/304 |
| 2007/0233022 A1 | 10/2007 | Henley et al. | |
| 2007/0260226 A1* | 11/2007 | Jaeb | A61M 1/0005 |
| | | | 604/543 |
| 2008/0103489 A1 | 5/2008 | Dahners | |
| 2008/0161778 A1 | 7/2008 | Steward | |
| 2008/0167593 A1 | 7/2008 | Fleischmann | |
| 2008/0195017 A1 | 8/2008 | Robinson et al. | |
| 2008/0200906 A1 | 8/2008 | Sanders et al. | |
| 2008/0208147 A1 | 8/2008 | Argenta et al. | |
| 2008/0243096 A1 | 10/2008 | Svedman | |
| 2008/0281281 A1 | 11/2008 | Meyer et al. | |
| 2008/0294147 A1 | 11/2008 | Radl et al. | |
| 2008/0300578 A1 | 12/2008 | Freedman | |
| 2008/0306456 A1 | 12/2008 | Riesinger | |
| 2009/0005744 A1 | 1/2009 | Karpowicz et al. | |
| 2009/0012501 A1 | 1/2009 | Boehringer et al. | |

(56) References Cited

U.S. PATENT DOCUMENTS

| | | | |
|---|---|---|---|
| 2009/0043268 A1* | 2/2009 | Eddy | A61M 1/0037 604/290 |
| 2009/0093778 A1 | 4/2009 | Svedman | |
| 2009/0099519 A1 | 4/2009 | Kaplan | |
| 2009/0124988 A1 | 5/2009 | Coulthard | |
| 2009/0126103 A1 | 5/2009 | Dietrich et al. | |
| 2009/0131892 A1 | 5/2009 | Karpowicz et al. | |
| 2009/0137973 A1 | 5/2009 | Karpowicz et al. | |
| 2009/0157016 A1 | 6/2009 | Adahan | |
| 2009/0171288 A1 | 7/2009 | Wheeler | |
| 2009/0204085 A1* | 8/2009 | Biggie | A61M 1/0088 604/313 |
| 2009/0227968 A1 | 9/2009 | Vess | |
| 2009/0264837 A1 | 10/2009 | Adahan | |
| 2009/0281526 A1 | 11/2009 | Kenny et al. | |
| 2009/0287133 A1* | 11/2009 | LaGreca, Sr. | A61F 13/00063 602/54 |
| 2009/0293887 A1 | 12/2009 | Wilkes et al. | |
| 2009/0299249 A1 | 12/2009 | Wilkes et al. | |
| 2009/0299251 A1 | 12/2009 | Buan | |
| 2009/0299255 A1 | 12/2009 | Kazala, Jr. et al. | |
| 2009/0299257 A1 | 12/2009 | Long et al. | |
| 2009/0299303 A1 | 12/2009 | Seegert | |
| 2009/0299308 A1 | 12/2009 | Kazala et al. | |
| 2009/0299340 A1 | 12/2009 | Kazala et al. | |
| 2009/0312723 A1* | 12/2009 | Blott | A61M 1/0058 604/290 |
| 2010/0036334 A1* | 2/2010 | Heagle | A61F 13/02 604/319 |
| 2010/0069850 A1 | 3/2010 | Fabo | |
| 2010/0069858 A1 | 3/2010 | Olson | |
| 2010/0069863 A1 | 3/2010 | Olson | |
| 2010/0069885 A1 | 3/2010 | Stevenson et al. | |
| 2010/0087767 A1 | 4/2010 | McNeil | |
| 2010/0094234 A1 | 4/2010 | Ramella et al. | |
| 2010/0106106 A1 | 4/2010 | Heaton et al. | |
| 2010/0106114 A1* | 4/2010 | Weston | A61M 1/0088 604/319 |
| 2010/0106121 A1* | 4/2010 | Holm | A61F 13/0203 604/368 |
| 2010/0125258 A1 | 5/2010 | Coulthard et al. | |
| 2010/0152639 A1 | 6/2010 | Miau et al. | |
| 2010/0160878 A1 | 6/2010 | Hunt et al. | |
| 2010/0160901 A1 | 6/2010 | Hu et al. | |
| 2010/0174250 A1* | 7/2010 | Hu | A61F 5/4401 604/319 |
| 2010/0185163 A1* | 7/2010 | Heagle | A61F 13/0203 604/290 |
| 2010/0191197 A1 | 7/2010 | Braga et al. | |
| 2010/0191198 A1 | 7/2010 | Heagle | |
| 2010/0210986 A1 | 8/2010 | Sanders | |
| 2010/0262091 A1 | 10/2010 | Larsson | |
| 2010/0305524 A1* | 12/2010 | Vess | A61M 1/0023 604/313 |
| 2010/0324510 A1 | 12/2010 | Andresen et al. | |
| 2010/0324516 A1* | 12/2010 | Braga | A61F 13/00 604/378 |
| 2011/0028290 A1 | 2/2011 | Ozawa | |
| 2011/0028919 A1 | 2/2011 | Johnnison et al. | |
| 2011/0125066 A1 | 5/2011 | Robinson et al. | |
| 2011/0130712 A1 | 6/2011 | Topaz | |
| 2011/0172582 A1* | 7/2011 | Darian | A61F 15/004 602/79 |
| 2011/0230849 A1* | 9/2011 | Coulthard | A61M 1/0088 604/319 |
| 2012/0116334 A1* | 5/2012 | Albert | A61F 13/02 604/319 |
| 2012/0143156 A1 | 6/2012 | Bannister et al. | |
| 2012/0302976 A1 | 11/2012 | Locke et al. | |
| 2013/0066284 A1* | 3/2013 | Croizat | A61M 1/0088 604/313 |
| 2013/0066286 A1* | 3/2013 | Croizat | A61M 1/0088 604/319 |
| 2013/0066365 A1* | 3/2013 | Belson | A61B 17/08 606/216 |
| 2013/0144230 A1* | 6/2013 | Wu | A61F 13/0216 604/319 |
| 2013/0172835 A1 | 7/2013 | Braga et al. | |
| 2013/0253453 A1 | 9/2013 | Olson | |
| 2013/0310809 A1* | 11/2013 | Armstrong | A61M 1/0088 604/543 |
| 2014/0343520 A1 | 11/2014 | Bennett et al. | |
| 2015/0073358 A1 | 3/2015 | Jaeb et al. | |

FOREIGN PATENT DOCUMENTS

| | | |
|---|---|---|
| DE | 20 2010 009 148 | 10/2010 |
| EP | 0 325 771 | 9/1993 |
| EP | 0 392 640 | 6/1995 |
| EP | 0 441 418 | 7/1995 |
| EP | 0 465 601 | 1/1997 |
| EP | 0 751 757 | 1/1997 |
| EP | 0 692 987 | 10/1997 |
| EP | 0 651 983 | 9/1998 |
| EP | 0 777 504 | 10/1998 |
| EP | 0 782 421 | 7/1999 |
| EP | 1 018 967 | 7/2000 |
| EP | 0 690 706 | 11/2000 |
| EP | 1 129 734 | 9/2001 |
| EP | 0 921 775 | 12/2001 |
| EP | 0 853 950 | 10/2002 |
| EP | 0 708 620 | 5/2003 |
| EP | 1 014 905 | 5/2003 |
| EP | 1 088 569 | 8/2003 |
| EP | 0 993 317 | 9/2003 |
| EP | 0 880 953 | 10/2003 |
| EP | 1 219 311 | 7/2004 |
| EP | 1 440 667 | 7/2004 |
| EP | 1 448 261 | 8/2004 |
| EP | 1 100 574 | 2/2005 |
| EP | 0 688 189 | 6/2005 |
| EP | 1 284 777 | 4/2006 |
| EP | 0 982 015 | 8/2006 |
| EP | 0 620 720 | 11/2006 |
| EP | 1 227 853 | 1/2008 |
| EP | 1 476 217 | 3/2008 |
| EP | 2 218 431 | 4/2008 |
| EP | 1 920 791 | 5/2008 |
| EP | 1 233 808 | 7/2008 |
| EP | 1 827 561 | 1/2009 |
| EP | 2 052 750 | 4/2009 |
| EP | 2 098 257 | 9/2009 |
| EP | 2 103 290 | 9/2009 |
| EP | 1 652 549 | 1/2010 |
| EP | 1 905 465 | 1/2010 |
| EP | 2 127 690 | 3/2010 |
| EP | 1 703 922 | 5/2011 |
| EP | 2 319 550 | 5/2011 |
| EP | 2 349 155 | 8/2011 |
| EP | 1 578 477 | 9/2011 |
| EP | 1 763 378 | 12/2011 |
| EP | 1 169 071 | 2/2012 |
| EP | 2 529 766 | 12/2012 |
| EP | 2 659 915 | 11/2013 |
| EP | 2 628 500 | 5/2014 |
| GB | 2307180 | 6/2000 |
| GB | 2336546 | 6/2000 |
| GB | 2344531 | 7/2000 |
| GB | 2356148 | 6/2004 |
| GB | 2431351 | 4/2007 |
| JP | H04-503625 | 7/1992 |
| JP | H08-098706 | 4/1996 |
| WO | WO 1994/03214 | 2/1994 |
| WO | WO 1994/21207 | 9/1994 |
| WO | WO 1994/23678 | 10/1994 |
| WO | WO 1999/001173 | 1/1999 |
| WO | WO 2000/07653 | 2/2000 |
| WO | WO 2000/61206 | 10/2000 |
| WO | WO 2000/064394 | 11/2000 |
| WO | WO 2001/85228 | 11/2001 |
| WO | WO 2001/85248 | 11/2001 |
| WO | WO 2002/043634 | 6/2002 |

(56) References Cited

FOREIGN PATENT DOCUMENTS

| | | |
|---|---|---|
| WO | WO 2002/070040 | 9/2002 |
| WO | WO 2003/086232 | 10/2003 |
| WO | WO 2003/101508 | 12/2003 |
| WO | WO 2004/018020 | 3/2004 |
| WO | WO 2004/037334 | 5/2004 |
| WO | WO 2004/041064 | 5/2004 |
| WO | WO 2004/060148 | 7/2004 |
| WO | WO 2005/009488 | 2/2005 |
| WO | WO 2005/016179 | 2/2005 |
| WO | WO 2005/025447 | 3/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/061025 | 7/2005 |
| WO | WO 2005/072789 | 8/2005 |
| WO | WO 2005/079718 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2005/105179 | 11/2005 |
| WO | WO 2005/105180 | 11/2005 |
| WO | WO 2005/107842 | 11/2005 |
| WO | WO 2005/115497 | 12/2005 |
| WO | WO 2005/115523 | 12/2005 |
| WO | WO 2005/123170 | 12/2005 |
| WO | WO 2006/046060 | 5/2006 |
| WO | WO 2006/052338 | 5/2006 |
| WO | WO 2006/052745 | 5/2006 |
| WO | WO 2006/114637 | 11/2006 |
| WO | WO 2006/114638 | 11/2006 |
| WO | WO 2006/114648 | 11/2006 |
| WO | WO 2007/006306 | 1/2007 |
| WO | WO 2007/013049 | 2/2007 |
| WO | WO 2007/013064 | 2/2007 |
| WO | WO 2007/015964 | 2/2007 |
| WO | WO 2007/016590 | 2/2007 |
| WO | WO 2007/019038 | 2/2007 |
| WO | WO 2007/030598 | 3/2007 |
| WO | WO 2007/030599 | 3/2007 |
| WO | WO 2007/030601 | 3/2007 |
| WO | WO 2007/031757 | 3/2007 |
| WO | WO 2007/031762 | 3/2007 |
| WO | WO 2007/031765 | 3/2007 |
| WO | WO 2007/041642 | 4/2007 |
| WO | WO 2007/062024 | 5/2007 |
| WO | WO 2007/067685 | 6/2007 |
| WO | WO 2007/085396 | 8/2007 |
| WO | WO 2007/087808 | 8/2007 |
| WO | WO 2007/087809 | 8/2007 |
| WO | WO 2007/087811 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/133618 | 11/2007 |
| WO | WO 2007/143060 | 12/2007 |
| WO | WO 2008/008032 | 1/2008 |
| WO | WO 2008/010094 | 1/2008 |
| WO | WO 2008/011774 | 1/2008 |
| WO | WO 2008/012278 | 1/2008 |
| WO | WO 2008/013896 | 1/2008 |
| WO | WO 2008/014358 | 1/2008 |
| WO | WO 2008/016304 | 2/2008 |
| WO | WO 2008/027449 | 3/2008 |
| WO | WO 2008/036162 | 3/2008 |
| WO | WO 2008/040020 | 4/2008 |
| WO | WO 2008/041926 | 4/2008 |
| WO | WO 2008/043067 | 4/2008 |
| WO | WO 2008/048527 | 4/2008 |
| WO | WO 2008/064502 | 6/2008 |
| WO | WO 2008/086397 | 7/2008 |
| WO | WO 2008/100437 | 8/2008 |
| WO | WO 2008/100440 | 8/2008 |
| WO | WO 2008/100446 | 8/2008 |
| WO | WO 2008/112304 | 9/2008 |
| WO | WO 2008/131895 | 11/2008 |
| WO | WO 2008/132215 | 11/2008 |
| WO | WO 2008/135997 | 11/2008 |
| WO | WO 2008/141470 | 11/2008 |
| WO | WO 2008/154158 | 12/2008 |
| WO | WO 2009/002260 | 12/2008 |
| WO | WO 2009/004370 | 1/2009 |
| WO | WO 2009/016603 | 2/2009 |
| WO | WO 2009/016605 | 2/2009 |
| WO | WO 2009/019229 | 2/2009 |
| WO | WO 2009/021047 | 2/2009 |
| WO | WO 2009/021353 | 2/2009 |
| WO | WO 2009/034322 | 3/2009 |
| WO | WO 2009/062327 | 5/2009 |
| WO | WO 2009/066104 | 5/2009 |
| WO | WO 2009/066106 | 5/2009 |
| WO | WO 2009/067711 | 5/2009 |
| WO | WO 2009/068665 | 6/2009 |
| WO | WO 2009/071926 | 6/2009 |
| WO | WO 2009/071929 | 6/2009 |
| WO | WO 2009/071932 | 6/2009 |
| WO | WO 2009/071933 | 6/2009 |
| WO | WO 2009/071935 | 6/2009 |
| WO | WO 2009/071948 | 6/2009 |
| WO | WO 2009/078790 | 6/2009 |
| WO | WO 2009/086580 | 7/2009 |
| WO | WO 2009/088925 | 7/2009 |
| WO | WO 2009/111655 | 9/2009 |
| WO | WO 2009/114624 | 9/2009 |
| WO | WO 2009/114760 | 9/2009 |
| WO | WO 2009/114790 | 9/2009 |
| WO | WO 2009/124473 | 10/2009 |
| WO | WO 2009/124548 | 10/2009 |
| WO | WO 2009/126102 | 10/2009 |
| WO | WO 2009/126103 | 10/2009 |
| WO | WO 2009/137194 | 11/2009 |
| WO | WO 2009/140376 | 11/2009 |
| WO | WO 2009/145703 | 12/2009 |
| WO | WO 2009/145894 | 12/2009 |
| WO | WO 2009/158125 | 12/2009 |
| WO | WO 2009/158126 | 12/2009 |
| WO | WO 2009/158127 | 12/2009 |
| WO | WO 2009/158129 | 12/2009 |
| WO | WO 2010/014177 | 2/2010 |
| WO | WO 2010/033271 | 3/2010 |
| WO | WO 2010/033272 | 3/2010 |
| WO | WO 2010/033769 | 3/2010 |
| WO | WO 2010/035017 | 4/2010 |
| WO | WO 2010/042240 | 4/2010 |
| WO | WO 2010/051071 | 5/2010 |
| WO | WO 2010/056977 | 5/2010 |
| WO | WO 2010/059712 | 5/2010 |
| WO | WO 2010/072395 | 7/2010 |
| WO | WO 2010/078166 | 7/2010 |
| WO | WO 2010/094957 | 8/2010 |
| WO | WO 2010/120470 | 10/2010 |
| WO | WO 2010/147533 | 12/2010 |
| WO | WO 2011/049562 | 4/2011 |
| WO | WO 2011/100851 | 8/2011 |
| WO | WO 2011/115908 | 9/2011 |
| WO | WO 2011/087871 | 10/2011 |
| WO | WO 2012/142002 | 10/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2013/043972 | 3/2013 |
| WO | WO 2013/123005 | 8/2013 |
| WO | WO 2014/066057 | 5/2014 |
| WO | WO 2014/043238 | 9/2014 |
| WO | WO 2014/158526 | 10/2014 |

OTHER PUBLICATIONS

International Search Report and Written Opinion for PCT/US2011/041521, dated Oct. 7, 2011.

(56) References Cited

OTHER PUBLICATIONS

Fleischmann et al., Vacuum Sealing: Indication, Technique, and Results, Eur J Orthop Surg Traumatol, (1995) 5:37-40.
Greer, et al., Techniques for Applying Subatmospheric Pressure Dressing to Wounds in Difficult Regions of Anatomy, JWOCN, vol. 26, No. 5, 1999 pp. 250-253.
Jeter, K. et al., "Managing Draining Wounds and Fistulae: New and Established Methods" Chronic Wound Care pp. 240-246, 1990.
KCI V.A.C. Granufoam Bridge Dressing Product Prochure (2009) in 2 pages.
International Search Report and Written Opinion for PCT/US2011/041521, dated Jun. 25, 2013.

\* cited by examiner

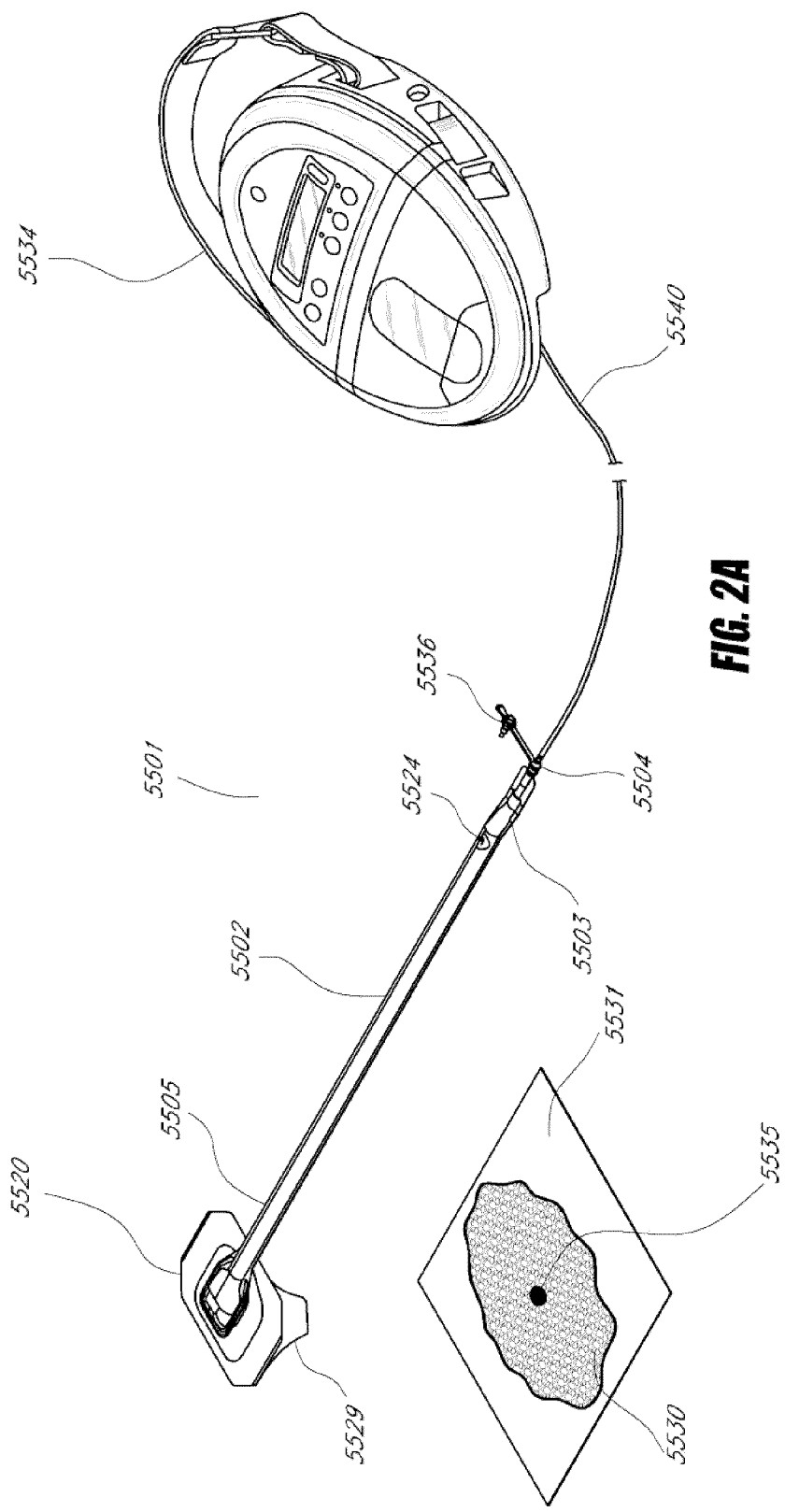

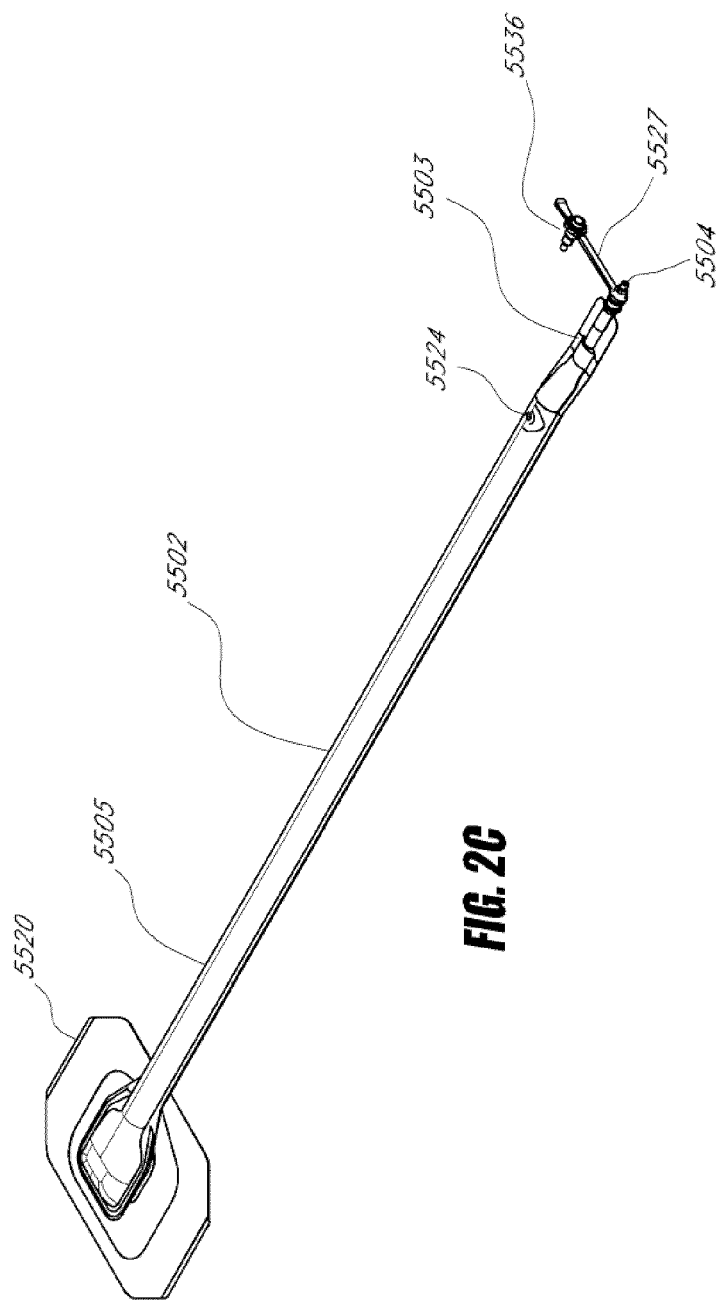

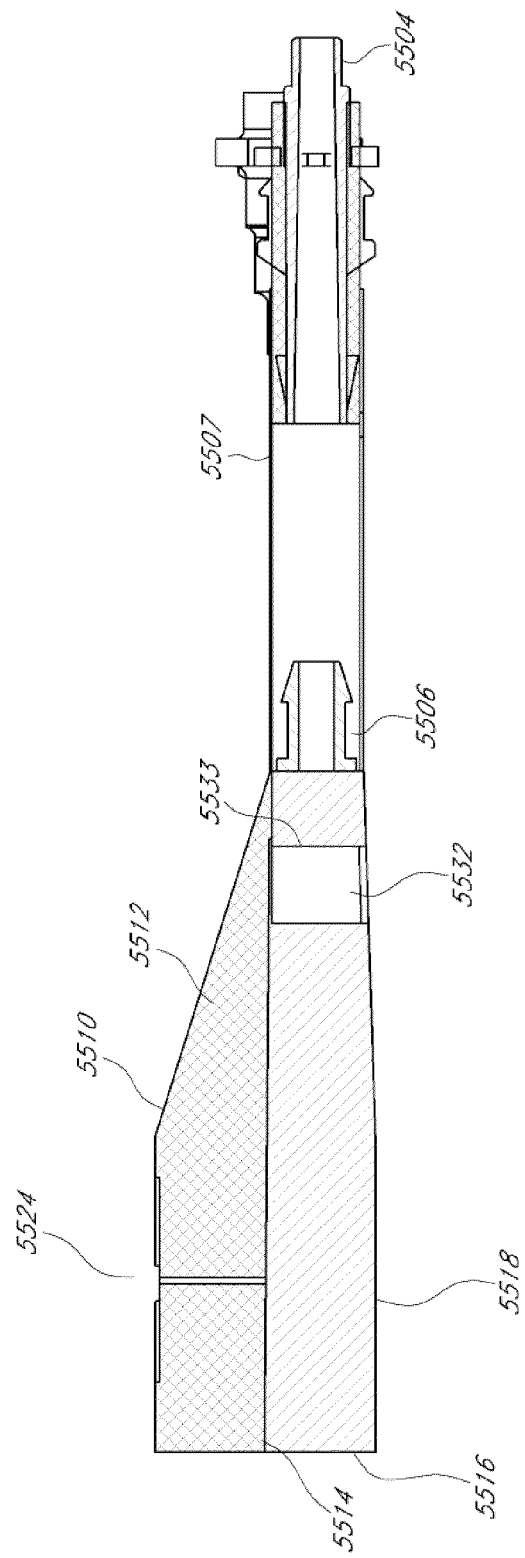

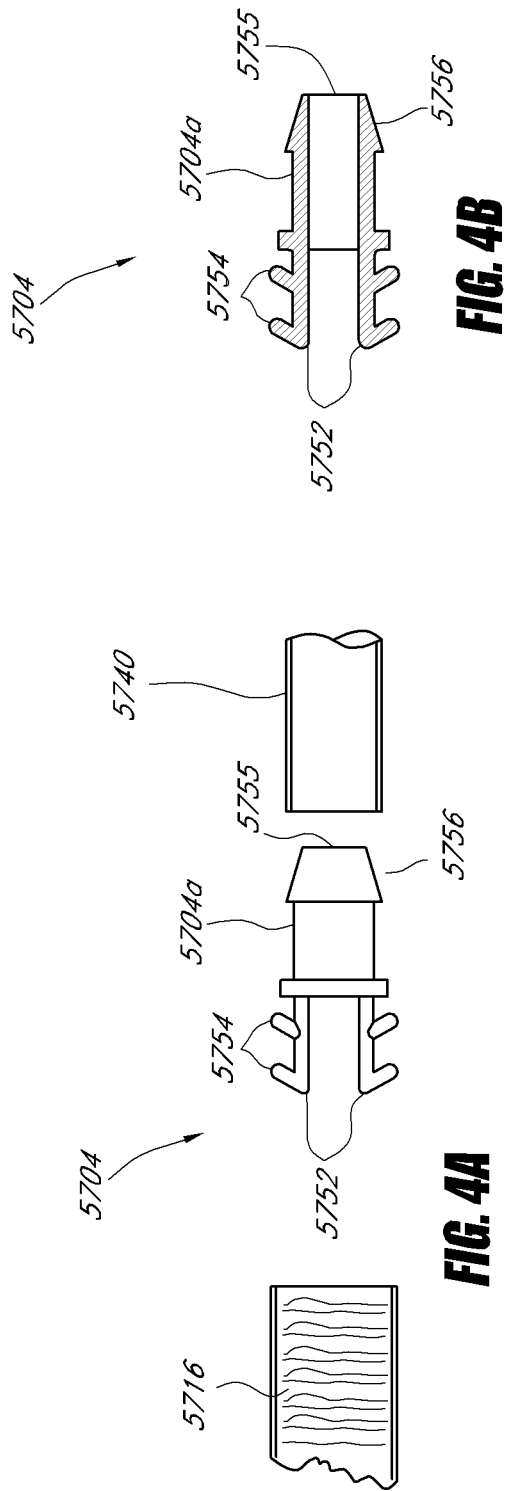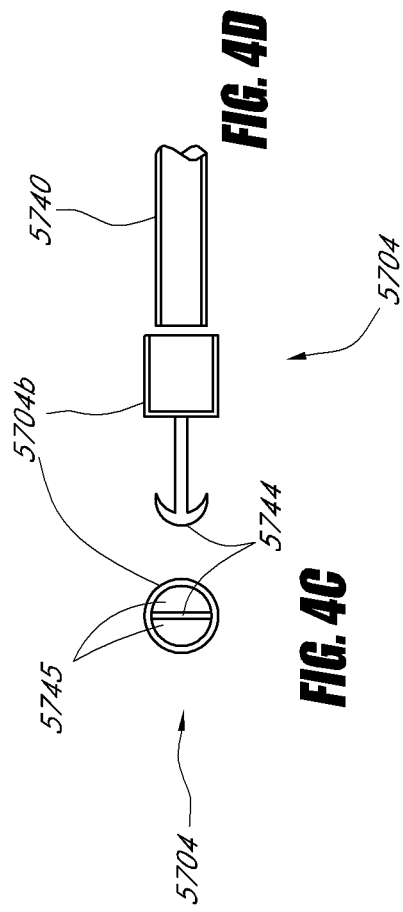

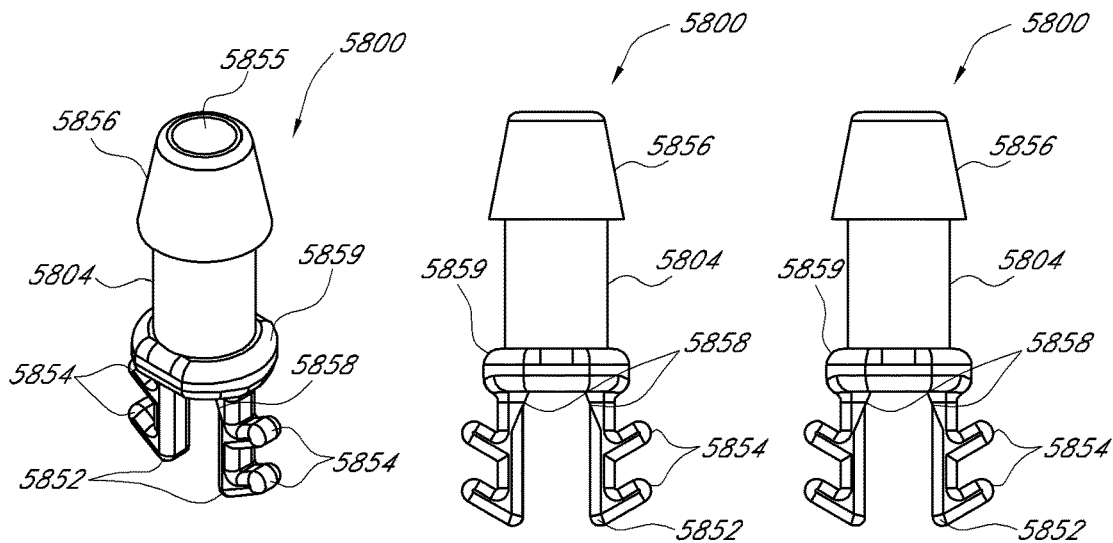
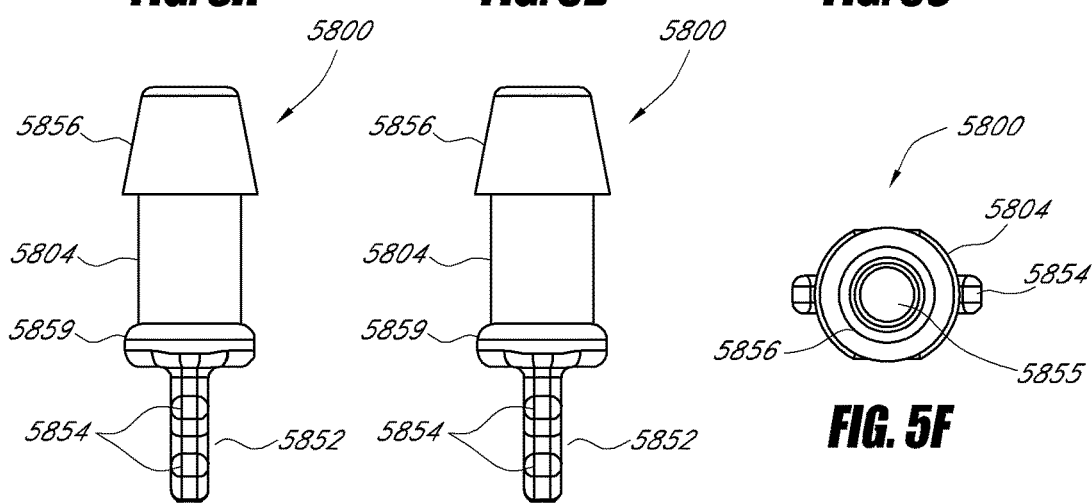
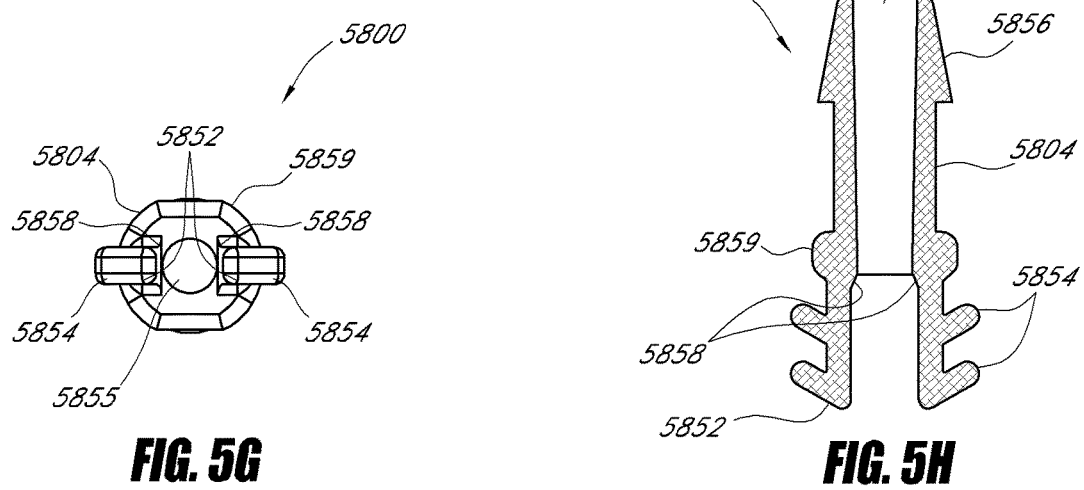

APPARATUSES AND METHODS FOR NEGATIVE PRESSURE WOUND THERAPY

CROSS REFERENCE TO RELATED APPLICATIONS

This application is a continuation of U.S. application Ser. No. 13/381,884, filed Jul. 12, 2013, which is a U.S. National Phase of the PCT International Application No. PCT/US2011/041521 filed on Jun. 22, 2011, designating the United States, which claims priority to U.S. Provisional Application Ser. No. 61/426,432, filed Dec. 22, 2010, the contents of which are incorporated herein in their entirety.

FIELD OF THE INVENTION

Embodiments of the present invention relate generally to the treatment of wounds using negative pressure wound therapy, and more specifically to an improved apparatus and method thereof.

BACKGROUND OF THE INVENTION

The treatment of open or chronic wounds that are too large to spontaneously close or otherwise fail to heal by means of applying negative pressure to the site of the wound is well known in the art. Negative pressure wound treatment systems currently known in the art commonly involve placing a cover that is impermeable to liquids over the wound, using various means to seal the cover to the tissue of the patient surrounding the wound, and connecting a source of negative pressure (such as a vacuum pump) to the cover in a manner so that an area of negative pressure is created under the cover in the area of the wound.

SUMMARY OF THE INVENTION

Embodiments of the invention disclosed herein are directed to a reduced pressure appliance and methods of treatment using a reduced pressure appliance, and may be useful in the treatment of wounds using reduced pressure.

Certain embodiments of the invention employ fluidic connectors and/or suction adapters for connecting a source of negative pressure to a dressing positioned over a wound site. These fluidic connectors and/or suction adapters offer advantages over the prior art. For example and for illustrative purposes only, some of the embodiments may offer a softer, kink-free fluidic connector for connecting a wound site to a source of negative pressure for treatment. Such a fluidic connector and/or suction adapter is faster to apply, requiring fewer steps compared to prior art connectors, and offers greater patient comfort and safety by being soft and conformable, thereby avoiding pressure ulcers and other complications caused by harder connectors.

Also disclosed herein are embodiments of an apparatus for providing suction to a wound site comprising a top and bottom layer constructed from a liquid-impermeable material with a 3D knitted or 3D fabric material located between these top and bottom layers and forming an elongate channel.

In another embodiment of a suction adapter, this adapter has an applicator with an upper and lower surface, with the upper surface connected to the distal end of a bridge. The bridge has a proximal end and a distal end, and has an upper fluid passage connected to an air leak and a lower fluid passage in fluid communication with a source of negative pressure, with the lower fluid passage comprising a 3D knitted or 3D fabric material.

In some embodiments of the suction adapter, the upper fluid passage may comprise foam. The bridge portion may further comprise a top layer, a bottom layer and an intermediate layer, each of the layers having proximal ends and distal ends and elongate portions extending therebetween, where the upper fluid passage extends between the top and intermediate layers, and the lower fluid passage extends between the intermediate and bottom layers. The distal end of the bridge may also have an enlarged shape. The air leak may be disposed at the proximal end of the bridge. The 3D knitted or 3D fabric material may include a top knitted layer, a bottom knitted layer, and a middle area with vertically extending fibers, and may be approximately 1.5 to 6 mm thick. The 3D knitted or 3D fabric material may be constructed so as to resist compression to less than half its original thickness when subjected to a load of 15 psi.

The suction adapter embodiments above may be used in embodiments of a negative pressure wound treatment system comprising a flexible drape configured to be positioned over a wound and sealed to the skin surrounding the wound, and where the suction adapter is configured to be attached to the drape so as to surround at least one aperture formed in the drape. A vacuum pump is preferably connected by at least one conduit to the suction adapter.

Methods of treating a wound with negative pressure are also disclosed herein. A method of treating a wound site with negative pressure comprises applying a flexible drape over a wound site, applying a flexible suction adapter over an opening in the flexible drape, where the flexible suction adapter comprises top and bottom layers constructed from a liquid-impermeable material, a 3D knitted or 3D fabric material located between the top and bottom layers, an aperture in the bottom layer in fluid communication with the wound site through the opening and the 3D knitted or 3D fabric material, and applying negative pressure to the wound, the negative pressure being transmitted to the wound through at least one conduit connected between the source of negative pressure and the flexible suction adapter and passing through the 3D knitted or 3D fabric material through the aperture in the bottom layer and into the opening in the flexible drape.

In some embodiments, the application of negative pressure to the wound may cause air to flow into the wound via an air leak disposed on the flexible suction adapter. The flow rate of air, may, in some embodiments be at least 0.08 liters/minute when negative pressure is applied to the suction adapter, and this flow rate may be maintained while a weight is placed on the suction adapter, for example a 4.75 kg weight. Adhesive may be placed on the suction adapter when adhering the adapter to the drape, or the adapter can be supplied pre-attached to a drape. Otherwise, the method above may comprise cutting an opening into the drape. Wound contact material can also be placed into the wound site prior to applying the drape. A similar method may transmit negative pressure to the wound through at least one conduit connected between the source of negative pressure and the flexible suction adapter and that passes through the 3D knitted material into the opening in the flexible drape.

In another embodiment, a negative pressure wound treatment system comprises a conduit, a suction adapter and a connector. The conduit is configured to deliver negative pressure to the wound from a source of negative pressure. The suction adapter is configured to deliver negative pressure to the wound, wherein the suction adapter comprises an elongate fluid channel having a proximal and a distal end and an elongate 3D knitted or 3D fabric material extending between the proximal and distal ends. A connector is configured to securely attach to a proximal portion of the 3D knitted or 3D fabric material, the connector being further configured to create a fluidic connection between the 3D knitted material in the elongate fluid channel and the conduit. In certain embodiments, the connector is configured to remain attached to the 3D knitted or 3D fabric material when subjected to a pulling force of less than 20 kg.

In some embodiments, the connector comprises two distally extending projections, each projection further comprising at least one barb located thereon, the barbs configured to be pushed into and be retained within a proximal portion of the 3D knitted or 3D fabric material. The connector may further comprise two distally extending projections, each projection further comprising at least one barb located thereon, the barbs configured to attach to upper and lower portions of the 3D knitted or 3D fabric material.

In other embodiments, the connector comprises a central distally extending projection configured to extend into the 3D knitted or 3D fabric material. The central projection may further comprise at least one barb.

In another embodiment, the connector comprises at least one opening configured to receive a pin or other locking device, and wherein the pin is pushed through at least a portion of the 3D knitted or 3D fabric material.

In another embodiment, the connector comprises a central channel and at least one lip configured to be pushed into and secured inside a proximal portion of the 3D knitted or 3D fabric material.

In another embodiment, the connector comprises at least one flexible line and one corresponding cavity configured to receive the at least one line, the line being configured to loop into a proximal portion of the 3D knitted or 3D fabric material. The line may further comprise at least one barb.

In another embodiment, a connector for connecting a fluid passage tube to a fabric channel is provided. The connector comprises a hollow cylindrical body comprising a central channel extending between a proximal end and a distal end of the hollow body. A plurality of projections extend distally from the hollow body. A plurality of barbs are provided on each of the projections, wherein the barbs are angled proximally, the barbs being configured to engage the fabric channel. A frustoconical lip at the proximal end of the hollow body is configured to be press-fit into the fluid passage tube. The connector is configured to withstand a pulling force of up to 20 kg before disengaging from the fabric channel.

In another embodiment, the connector for connecting a fluid passage tube to a fabric channel comprises a body having a proximal end and a distal end. At least one member extends distally from the body, the at least one member configured to extend into the fabric channel. The proximal end of the body is configured to be press-fit with an inner or outer surface of the fluid passage tube.

In some embodiments, the body may be cylindrical and/or hollow. The at least one member may comprise a plurality of projections, and the projections may additionally comprise one or more barbs extending in a proximal direction. The member may alternatively comprise at least one flexible line, and wherein the line comprises a tapered tip configured to loop through the fabric channel and be received and securely connected to a cavity formed in the connector. The proximal end of the body may comprise a frustoconical lip.

In another embodiment, a fluidic connection is provided, comprising any of the aforementioned connectors. A fabric channel is engaged with the proximal end of the connector. A tube is engaged with the distal end of the connector.

In another embodiment, a method of transporting fluid. The method comprises providing an elongate fluid channel comprising a 3D knitted or 3D fabric material. A connector is attached to the 3D knitted or 3D fabric material, wherein a distal end of the connector engages the 3D knitted or 3D fabric material. A conduit is attached to a proximal end of the connector. Fluid is transported through the 3D knitted or 3D fabric material, through the connector and through the conduit.

In some embodiments, the transporting of fluid comprises applying negative pressure to the conduit, the connector and the 3D knitted or 3D fabric material. The 3D knitted or 3D fabric material may be placed in fluid communication with a wound, wherein applying negative pressure comprises transmitting negative pressure through the conduit, the connector and the 3D knitted or 3D fabric material to the wound. In one embodiment, pulling on the connector with a force less than 20 kg does not dislodge the connector from the 3D knitted or 3D fabric material.

BRIEF DESCRIPTION OF THE DRAWINGS

FIG. 2A illustrates an embodiment of a negative pressure wound treatment system comprising a pump, and illustrating a flexible suction adapter being applied to a wound.

FIG. 2C illustrates an isometric view of a flexible suction adapter that may be used in a negative pressure wound treatment system.

FIG. 2F illustrates a close-up cutaway view of the proximal end of the flexible suction adapter of FIG. 2C.

FIGS. 4A-B illustrate an embodiment of a connector with two or more projections and that may be connected to a suction adapter illustrated in FIG. 2.

FIGS. 4C-D illustrate an embodiment of a connector with a distally-extending barb.

FIGS. 5A-G illustrate, respectively, front perspective, front, back, left side, right side, top and bottom views of an embodiment of a connector with two or more projections.

FIG. 5H illustrates a cross-section of the embodiment of FIGS. 5A-5G.

FIG. 5I illustrates a view of the connector of FIGS. 5A-5H being connected into a suction adapter as illustrated in FIG. 2A.

DETAILED DESCRIPTION OF THE PREFERRED EMBODIMENTS

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using reduced pressure. Wounds include, but are not limited to, open wounds, pressure sores, ulcers and burns. Treatment of such wounds can be performed using negative pressure wound therapy, wherein a reduced or negative pressure can be applied to the wound to facilitate and promote healing of the wound. It will also be appreciated that the negative pressure systems and methods as disclosed herein may be applied to other parts of the body, and are not necessarily limited to treatment of wounds.

Figure 1:
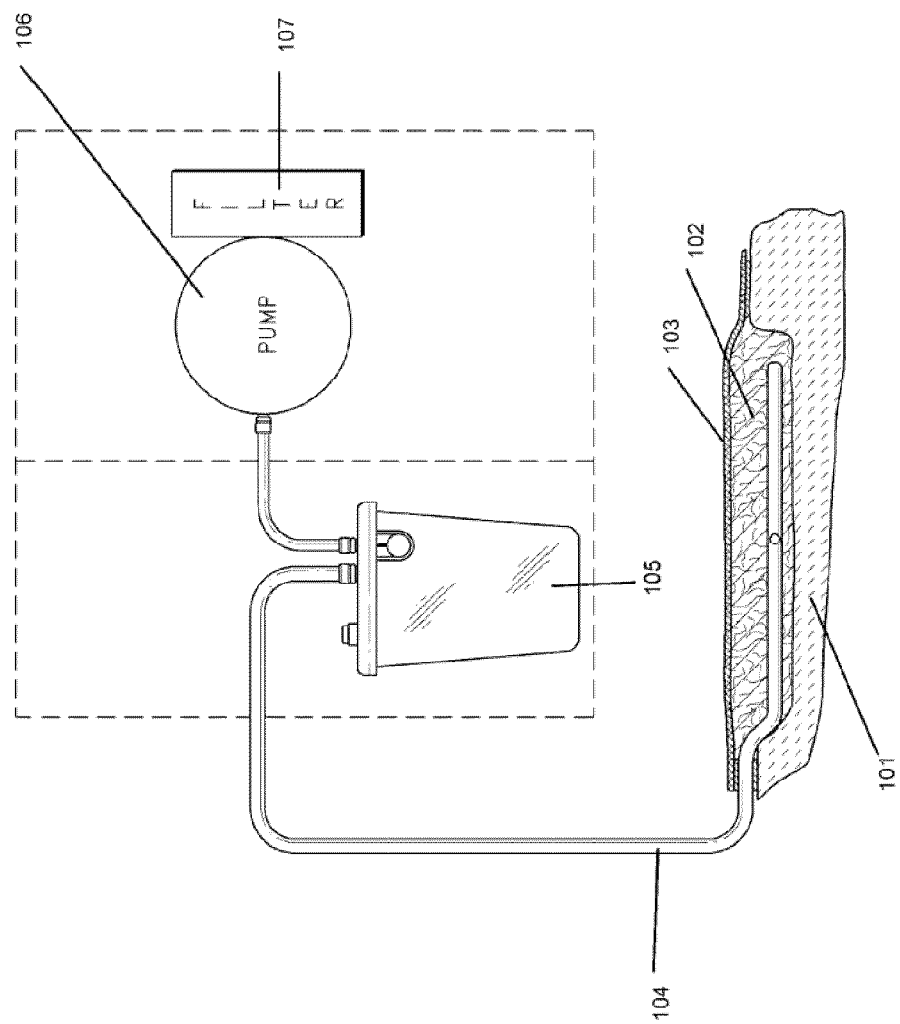
FIG. 1 illustrates a negative-pressure system that can be used in the treatment of wounds.

With reference initially to FIG. 1, treatment of a wound with negative pressure in certain embodiments of the application uses a system as illustrated schematically. In one embodiment, a wound 101 may be partly or completely filled with a wound packing material 102, such as foam, gauze, or any other suitable material. Alternatively, no wound packing material may be utilized. A flexible drape 103 that is at least partially fluid impermeable, and preferably liquid impermeable, may then be laid over the wound packing material 102 and preferably onto at least part of the surrounding healthy skin surrounding a wound. The drape 103 may be connected via a conduit 104 such as a flexible tube to a source of negative pressure 106 such as a pump. This conduit 104 may, in some embodiments, comprise one or more tubes. Suitable sources for negative pressure include both powered negative pressure sources such as vacuum pumps, and manually powered negative pressure sources such as suction bulbs. Negative pressure is applied to the wound through the conduit 104 and through the wound packing material 102, and wound exudate and other secretions are drawn away from the wound, through the wound packing material, and into a canister or other collection unit 105. The collection unit 105 may be located along the conduit before the negative pressure source, or may be located elsewhere relative to the negative pressure source. In some embodiments, one or more filters 107 may be provided along the vacuum pathway, for example at the outlet of the pump. This filter 107 may be useful for absorbing odors or may be a bacterial filter. Suitable systems for treating wounds in the above manner include the RENASYS-F, RENASYS-G, RENASYS EZ and RENASYS GO systems available from Smith & Nephew.

The application of reduced or negative pressure to a wound in the above manner may be used to promote faster healing, increase blood flow, decrease bacterial burden, increase the rate of granulation tissue formation, remove exudate and slough from the wound, alleviate interstitial edema, stimulate the proliferation of fibroblasts, stimulate the proliferation of endothelial cells, close chronic open wounds, inhibit burn penetration, and enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached.

Suitable drapes such as those used in the embodiments described herein are preferably liquid tight, such that at least partial negative pressure may be maintained at the wound site. The drape may be constructed from, for example, transparent flexible plastics such as polyurethane. Other suitable materials include without limitation synthetic polymeric materials that do not absorb aqueous fluids, including polyolefins, such as polyethylene and polypropylene, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. Lastly, although several embodiments illustrated herein illustrate an operator cutting an aperture into a drape manually, drapes used in the embodiments disclosed here may also be provided with one or more pre-cut apertures.

The wound is optionally filled with a wound packing material. Preferably, this wound packing material is conformable to the wound bed. This material is preferably soft and resiliently flexible. Examples of suitable forms of such wound fillers are foams formed of a suitable material, e.g. a resilient thermoplastic. Preferred materials for the present wound dressing include reticulated polyurethane foams with small apertures or pores and open-celled foams. Other suitable materials may include gauze. Preferably, such wound packing material will be able to channel wound exudate and other fluids through itself when negative pressure is applied to the wound. Some wound packing materials may include preformed channels or openings for such purposes.

Typically, the negative pressure wound treatment system is operated until a wound has reached a level of healing acceptable to a physician. The treatment system is preferably operated using a negative or reduced pressure ranging from about 40 to 200 mm Hg, though the amount may be lower or higher depending on physician preference. The time period for use of the wound treatment apparatus on a wound is selected by the physician. During the time period that negative pressure is applied, dressing changes and other temporary interruptions to the treatment may occur. Preferably, the negative pressure wound treatment system is able to handle at least 1 L of wound exudate or other fluid per day, or 0.694 ml/min. Some embodiments may handle over 10 L of wound exudate per day.

In preparing a wound site for treatment with the embodiments described herein, the wound is typically cleaned, debrided, and dried in a medically-acceptable manner. Optionally, the wound site may be filled partly or completely with a wound packing material 102 as shown in FIG. 1, including for example but without limitation gauze or foam.

This wound packing material may be trimmed to fit into the wound space. Next, a drape 103 is placed to cover the wound site while overlapping onto the healthy skin surrounding the wound; in some cases, the drape may need to be trimmed to size. Depending on the type of drape, a skin sealant may need to be applied to the skin surrounding the wound prior to placing the drape so that the drape may be adhered to the skin. Preferably, the drape 103 has an adhesive layer on its wound-facing side. Once adhered to the skin, the drape should form an air-tight seal against the skin. In order to treat the wound using negative pressure, some embodiments disclosed herein may require that the drape be pierced (for example to insert a conduit or to communicate with a suction adapter as described below) to create an aperture leading to the wound site. Obviously, some drapes may have an aperture or apertures already pre-cut or preformed into the drape, and some embodiments disclosed herein may not require an aperture to be made (as shown in FIG. 1). After application of negative pressure to the wound site, wound exudate and other fluids may be drawn away from the wound site and into a suitable receptacle 105, preferably interposed between the wound site and the source of negative pressure 106. Application of negative pressure is continued (with intervening dressing changes, if necessary) until the wound has reached a desired level of healing.

Figure 2B:
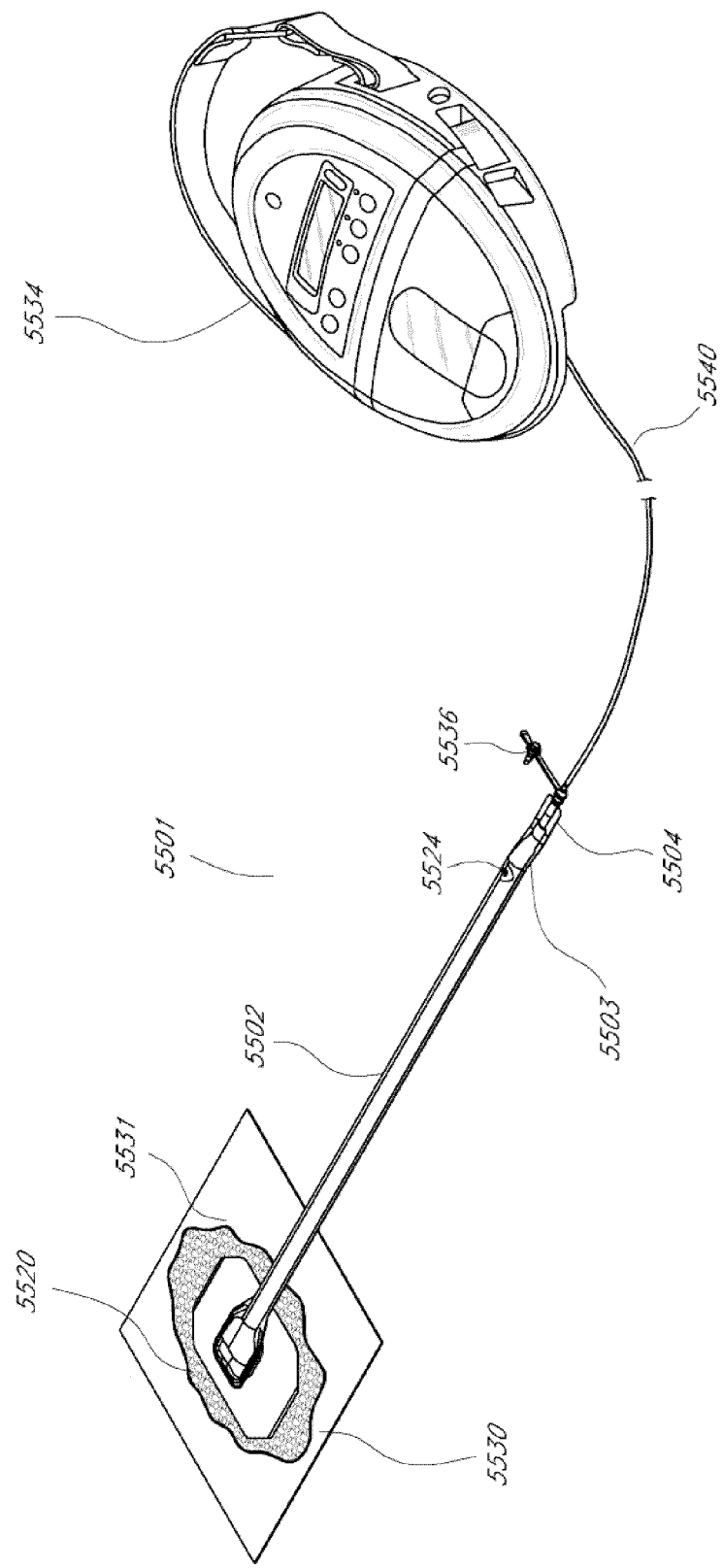
FIG. 2B illustrates the embodiment of FIG. 2A, with the flexible suction adapter having been placed over a wound.
Figure 2D:
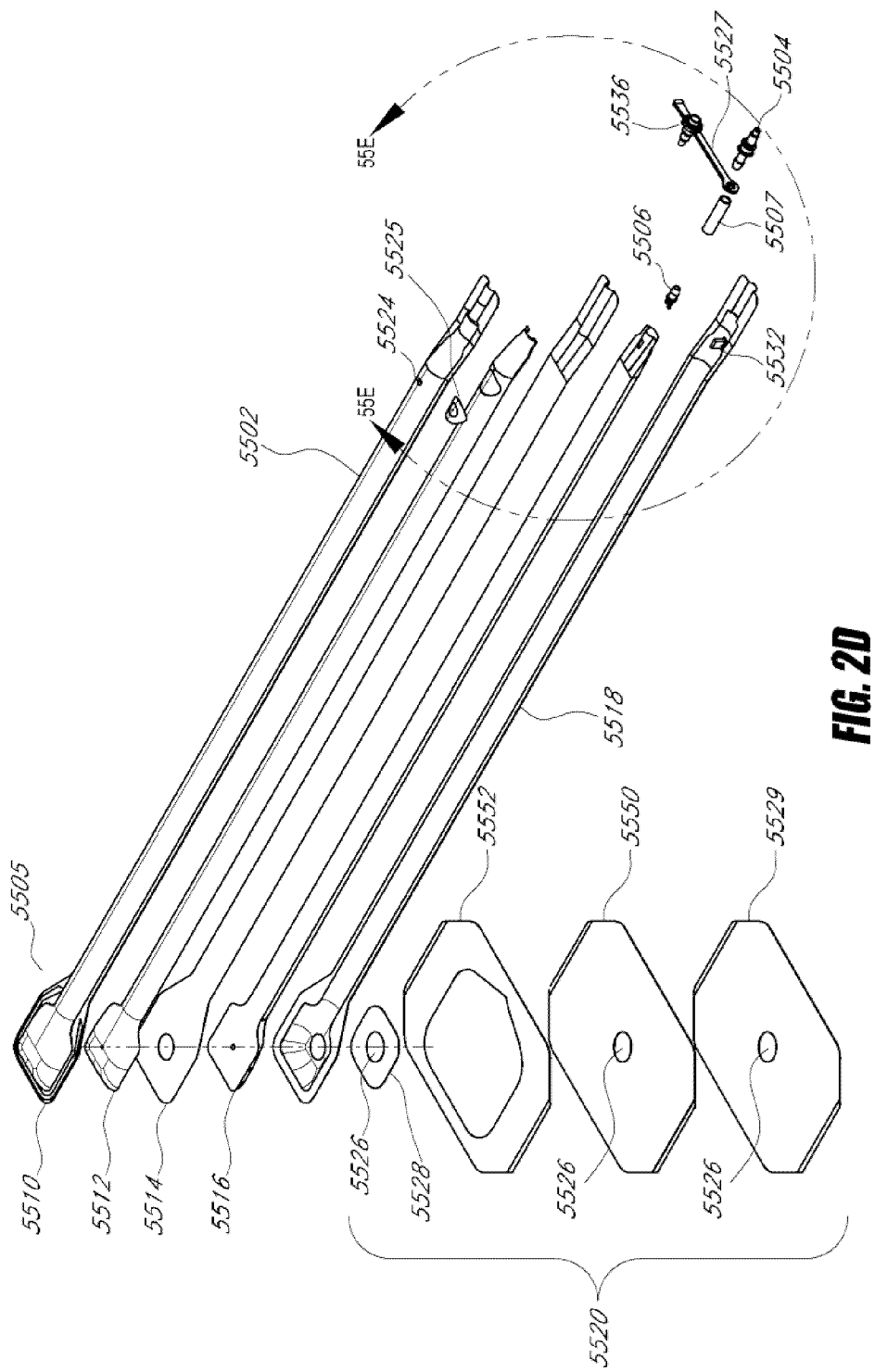
FIG. 2D illustrates an exploded view of the flexible suction adapter of FIG. 2C.

FIGS. 2A-J illustrate embodiments of a negative pressure wound treatment system 5501. Here, the system 5501 may comprise a bridge 5502 having a proximal end 5503 and a distal end 5505 and an applicator 5520 at the distal end 5505 of the bridge 5502 forming a flexible suction adapter. Preferably, the system 5501 comprises a bridge 5502. A connector 5504 is preferably disposed at the proximal end 5503 of the bridge 5502, so as to connect to at least one of the channels 5512 and/or 5516, as shown in FIG. 2D. A cap 5536 may be provided with the system 5501 (and can in some cases, as illustrated, be attached to the connector 5504). The cap 5536 can be useful in preventing fluids from leaking out of the proximal end 5503. In some embodiments, the connector 5504 may be an MQC Series™ quick connector, as sold by Value Plastics (Fort Collins, Colo.). The system 5501 may include a source of negative pressure such as a pump or negative pressure unit 5534 capable of supplying negative pressure. The pump also preferably comprises a canister or other container for the storage of wound exudates and other fluids that may be removed from the wound. In some embodiments, this pump 5534 can be a RENASYS GO pump, as sold by Smith & Nephew. The pump 5534 may be connected to the connector 5504 via a tube 5540. In use, the applicator 5520 is placed over an aperture 5535 formed in a drape 5531 that is placed over a suitably-prepared wound 5530, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

Here, and with particular reference to FIGS. 2C-D, the system 5501 may comprise a bridge 5502 having a proximal end 5503 and a distal end 5505 and an applicator 5520 at the distal end 5505 of the bridge 5502. In some embodiments, the bridge 5502 may comprise an upper channel layer 5512 positioned between an upper layer 5510 and an intermediate layer 5514, with a lower channel layer 5516 positioned between the intermediate layer 5514 and a bottom layer 5518. Preferably, the layers 5510, 5514, and 5518 have elongate portions extending between proximal and distal ends and may be comprised of a material that is fluid-impermeable, for example polymers such as polyurethane. It will of course be appreciated that the layers 5510, 5514, and 5518 may each be constructed from different materials, including semi-permeable materials. As illustrated in FIG. 2D, the upper and lower layers 5510 and 5518 may be curved, rounded or outwardly convex over a majority of their lengths. During assembly, for example, the layers 5510, 5514, and 5518 may be pinched together to weld or adhere the layers together. In doing so, the proximal ends of the channels 5512 and 5516 may be sandwiched between these layers, thus partially compressing the proximal ends of the channels 5512, 5516 and stretching the layers 5510, 5514, 5518 over these aforementioned proximal ends. Of course, the proximal ends of the materials used in the bridge section 5502 may not necessarily be rounded or curved; as shown in FIG. 2J, they can remain substantially squared off and straight.

The upper and lower channel layers 5512 and 5516 are preferably elongate layers extending from the proximal end 5503 to the distal end 5505 and may each preferably comprise a porous material, including for example open-celled foams such as polyethylene or polyurethane. In some embodiments, one or more of the upper and lower channel layers 5512 and 5516 may be comprised of a fabric, for example a knitted or woven spacer fabric (such as a knitted polyester 3D fabric, Baltex 7970®, or Gehring 879®) or a nonwoven material. Suitable materials may also include terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure and/or vented air to the wound site, and may also confer a degree of kinking or occlusion resistance to the channel layers 5512 and 5516 as described below. In one embodiment, the upper channel layer 5512 may comprise an open-celled foam such as polyurethane, and the lower channel layer may comprise a fabric as described herein. In another embodiment, the upper channel layer is optional, and the system may instead be provided with an open upper channel. In the embodiment illustrated in FIG. 2D, the upper channel layer 5512 may have a curved, rounded or upwardly convex upper surface and a substantially flat lower surface, and the lower channel layer 5516 may have a curved, rounded or downwardly convex lower surface and a substantially flat upper surface.

In some embodiments, the fabric may have a three-dimensional structure, where one or more types of fibers form a structure where the fibers extend in all three dimensions. Such a fabric may in some cases aid in wicking, transporting fluid, and/or transmitting negative pressure. To prevent the channels 5512 and/or 5516 from being displaced or twisted while encased in the system 5501—which may impair performance of the respective channels under negative pressure—it may in some embodiments be preferable to adhere or otherwise secure the channels 5512 and/or 5516 to one or more of the layers 5510, 5514, and 5518. In certain embodiments, these materials remain open and capable of communicating negative pressure to a wound area under the typical pressures used in negative pressure therapy, for example between 40 to 150 mmHg, although higher and lower values are possible. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Additionally, and as described previously, the materials used in the system 5501 are preferably conformable and soft, which may help to avoid pressure ulcers and other complications which may result from a wound treatment system being pressed against the skin of a patient. Further examples of 3D fabrics are discussed below in FIGS. 3A-C.

Preferably, the distal ends of the layers 5510, 5514, and 5518 and the channel layers 5512 and 5516 are enlarged at their distal ends (to be placed over a wound site), and may form a "teardrop" or other enlarged shape. The distal ends of at least the layers 5512, 5514, 5516, and 5518 may also be provided with at least one through aperture. This aperture may be useful not only for the drainage of wound exudate and for applying negative pressure to the wound, but also during manufacturing of the device, as these apertures may be used to align these respective layers appropriately.

Figure 2E:
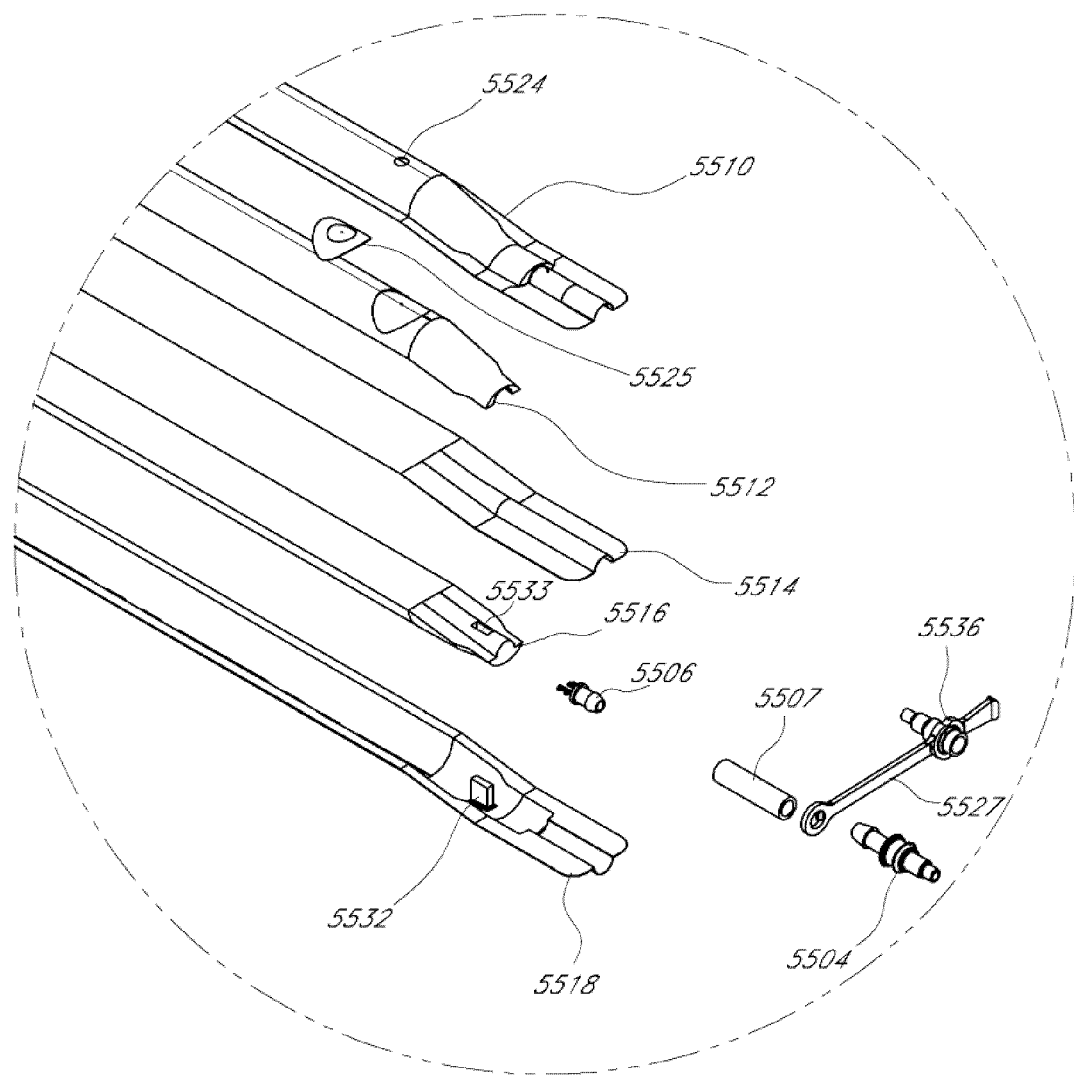
FIG. 2E illustrates a close-up view of the proximal end of the flexible suction adapter of FIG. 2D.
Figure 2G:
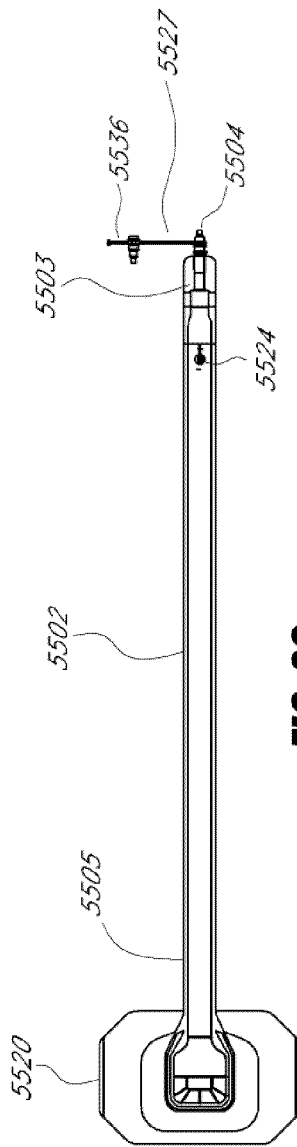
FIG. 2G illustrates a top view of the flexible suction adapter of FIG. 2C.
Figure 2H:
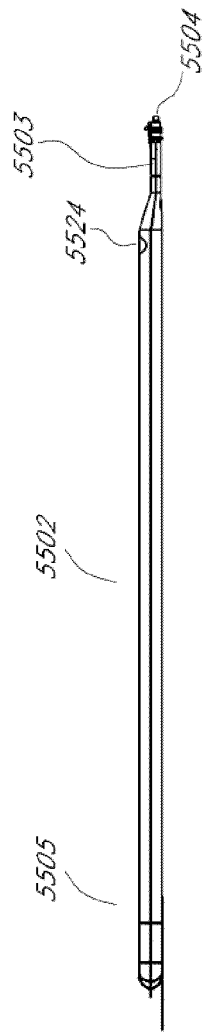
FIG. 2H illustrates a side view of the flexible suction adapter of FIG. 2C.
Figure 2I:
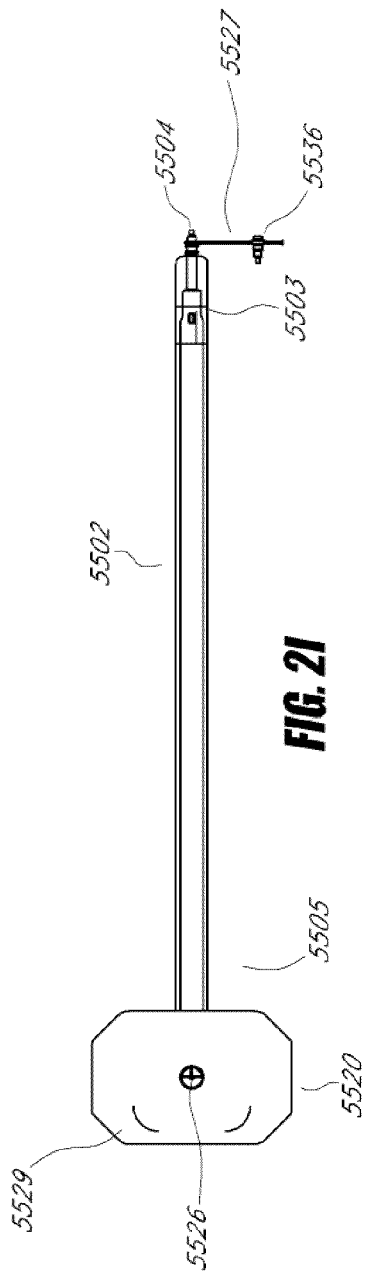
FIG. 2I illustrates a bottom view of the flexible suction adapter of FIG. 2C.
Figure 2J:
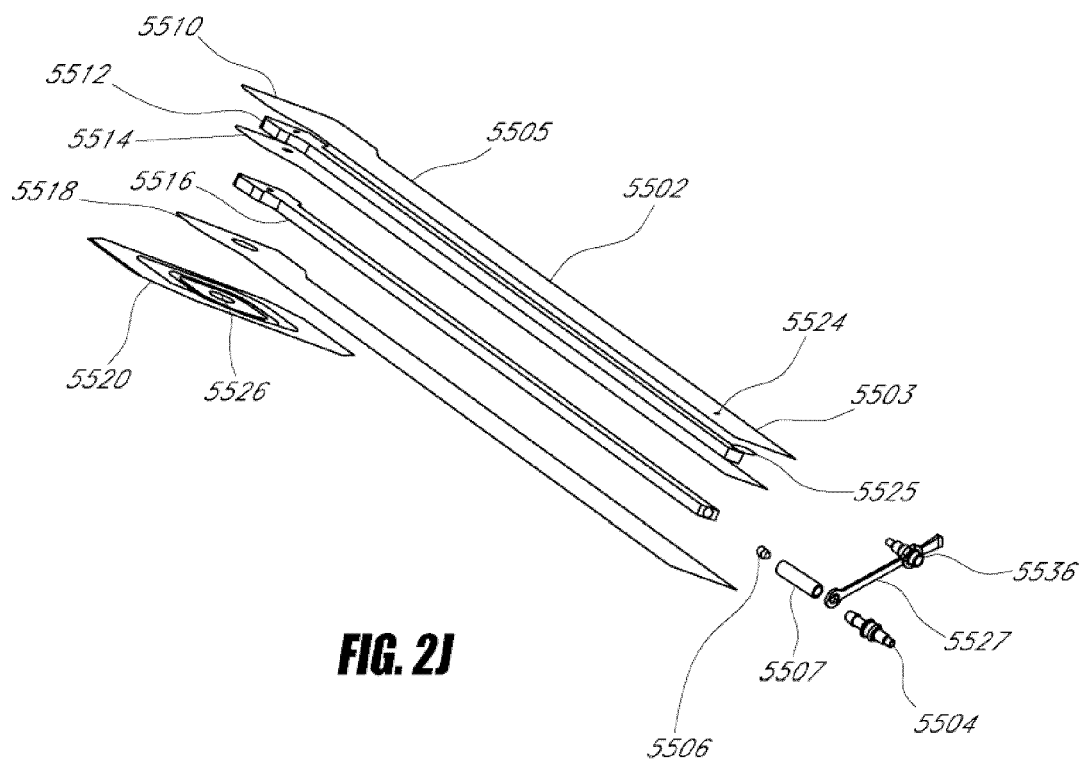
FIG. 2J illustrates an exploded view of an alternative flexible suction adapter.

With additional reference to FIGS. 2D-E and J, a channel connector 5506 is provided at the proximal end 5503 of the bridge 5502, the channel connector 5506 preferably being configured so as to be embedded into the lower channel layer 5516 so as to create a secure fluidic connection. The channel connector 5506 may in some embodiments be inserted into a pre-made cavity formed into the channel 5516; as illustrated in FIG. 2J, this cavity can be cut out or can be in the form of a rabbet joint. In some embodiments, the channel connector 5506 may be one of the connectors described in FIGS. 4A-L below. With one end of the channel connector 5506 being embedded into the lower channel layer 5516, the other end of the channel connector 5506 may be connected or in communication with, in one embodiment, a connector tube 5507, although in some embodiments the channel connector 5506 may be connected directly to the connector 5504, or else connected directly to a tube 5540 connected to a source of negative pressure. When using a connector tube 5507, the resulting assembly can permit a connector 5504 to be attached thereto. A cap 5536, which may be secured to the suction adapter for example via a cap leash 5527 secured with a ring disposed on the outer surface of the connector tube 5507. The cap 5536 may be used to cover the end of the suction adapter, for example at the connector 5504, so as to prevent exudate and other wound fluids from leaking out. The connector 5504 is preferably configured to connect with a tube 5540 connected to a source of negative pressure. The connector 5504 may for example comprise a lip or other such structure to aid in securing the connector 5504 to a tube 5540 and/or cap 5536, although it will be understood that other connector types are possible, including quick-disconnect couplings, luer locks, Christmas-tree, and other such connectors.

The upper layer 5510 may comprise additional material extending downward, preferably at least of the thickness of the bridge 5502; this material may then be used to bond or weld to the other layers so to form a fluid-tight seal. More specifically, during assembly, the upper layer 5510 may be attached, for example by melting, welding, or with adhesives, to the lower layer 5518 so as to form a fluid-tight seal (with the exception of the apertures at the distal and proximal ends). Preferably, the middle layer 5514 is attached to the top layer 5510 and the bottom layer 5518. In some embodiments, it may be preferable to attach or bond the connectors 5504 and/or 5506, as well as the tube 5507 to at least one of the layers 5510, 5514, 5518 so as to create a fluid-tight connection. To provide for a more secure connection, some embodiments may also be provided with a weld 5532 made onto the lower layer 5518. The lower channel 5516 may have a hole or aperture made through it, which may be used to weld it, via the weld 5532, to the lower layer 5518. This welding of the lower channel 5516 to the lower layer 5518 via the weld 5532 made through the hole 5533 may thus aid in preventing the various layers and channels from shifting or being displaced. Obviously, it will be understood that other securement means may be used, for example adhesives and the like, and that such arrangements may be also be used in the upper channel 5512.

In certain embodiments, for example as illustrated in FIGS. 2C-J, a controlled air leak 5524 may be disposed on the bridge portion 5502, for example at the proximal end thereof. This air leak 5524 may comprise an opening or channel extending through upper layer 5510, such that the air leak 5524 is in fluidic communication with the upper channel 5512. Upon the application of suction to the system 5501, air will enter through the air leak 5524 and move from the proximal end 5503 to the distal end 5505 along the upper channel 5512. The air will then be suctioned into the lower channel 5516 by passing through the apertures through the distal ends of the layers 5512, 5514, 5516 and 5518. The air leak 5524 preferably comprises a filter 5525. Preferably, the air leak 5524 is located at the proximal end of the bridge portion 5502 so as to minimize the likelihood of wound exudate or other fluids coming into contact and possibly occluding or interfering with the air leak 5524 or its filter 5525. In some embodiments, this filter 5525 is a microporous membrane capable of excluding microorganisms and bacteria, and which may be able to filter out particles larger than 45 μm. Preferably, the filter 5525 can exclude particles larger than 1.0 μm, and more preferably, particles larger than 0.2 μm. Advantageously, some embodiments may provide for a filter 5525 that is at least partially chemically-resistant, for example to water, common household liquids such as shampoos, and other surfactants. In some embodiments, reapplication of vacuum to the system 5501 and/or wiping of the exposed outer portion of the filter 5525 may be sufficient to clear any foreign substance occluding the filter 5525. The filter 5525 may be composed of a suitably-resistant polymer such as acrylic, polyethersulfone, or polytetrafluoroethylene, and may be oleophobic and/or hydrophobic. In some embodiments, the filter 5525 may also comprise a supporting backing layer, for example a nonwoven polyester support. Preferably, the air leak 5524 will supply a relatively constant air flow that does not appreciably increase as additional negative pressure is applied to the system 5501. In embodiments of the system 5501 where the air flow through the air leak 5524 increases as additional negative pressure is applied, preferably this increased air flow will be minimized and not increase in proportion to the negative pressure applied thereto.

The filter 5525 provided in the controlled air leak 5524 in certain embodiments may be useful in a system 5501 for use with more ambulatory and active patients. For example, a chemically-resistant filter may permit a patient to bathe or shower without damaging the filter's functionality when reconnected to a source of negative pressure. Any occlusion or fluid blocking the air leak 5524 could then be cleared by, for example, wiping off the filter 5525 or re-applying negative pressure to the system 5501. Such a system would also have the advantage that the system 5501 and any assorted wound dressing materials, if present, would not need to be removed and then re-applied should a patient need to be disconnected from the source of negative pressure, for example incidental to bathing. This would entail significant advantages in improving the cost-effectiveness and ease of use of the present treatment system.

The system 5501 is preferably constructed so as to provide a consistent fluid flow even if the system 5501 is kinked or weighted down. For example, in use on a patient, the bridge portion 5502 may become folded over itself, or else the patient may roll over, thus placing his or her weight over at least a portion of the system 5501. Typically, prior art dressings and fluidic connectors become blocked or ineffective in such situations and in some cases may contribute to complications such as pressure ulcers. Here, however, certain embodiments provide for improved blockage resistance if kinked or weighed down. Preferably, by employing channel layers 5512 and 5516 as described above, and more preferably by employing a foam channel layer 5512 and a fabric channel layer 5516, the system 5501 is able to maintain a flow rate through the air leak 5524 of at least 0.08 L/min, and preferably 0.12 L/min while negative pressure is applied through a source of negative pressure. Further embodiments also provide for the system 5501 to be able to handle fluid exudate drainage from the wound site through the lower channel 5516 of at least 10 L/day, or 6.9 ml/min. Certain embodiments provide for the system 5501 to maintain these flow rates with a weight, for example a 12 kg weight, pressing down on the bridge portion through a rod with a 1 in. diameter. In some embodiments, these flow rates are also maintained while the bridge portion 5502 is kinked over itself with the same weight, or for example with a 4.75 kg weight placed directly on the folded region. It is preferable that the system 5501 be able to withstand being folded or kinked over even during an extended period of time, for example over 40 hours, and not show any degradation in performance (e.g., flow rates) compared to its performance prior to being folded or kinked over. Preferably, embodiments of the system 5501 are also able to transmit and maintain a negative pressure at the wound that is close to the negative pressure level at the source of negative pressure. For example, an acceptable level of pressure maintained at the wound may be within ±25 mmHg of the negative pressure set at the source of negative pressure, with this pressure being preferably maintained at this level within 95% of the time that the system 5501 has negative pressure applied to it. Acceptable pressure levels may include pressure ranges between 40-120 mmHg, although levels of 200 mmHg have successfully been used.

With additional reference to FIGS. 2A-D, G-J, the system 5501 also comprises an applicator 5520 designed for placement over a wound site. Preferably, the applicator 5520 comprises a flexible layer 5550, for example polyethylene or polyurethane, with a layer of adhesive on its lower (wound-facing) side. Optionally, a protective release layer 5529 may be placed on the adhesive layer, which is removable before use. In some embodiments, a more rigid removable backing layer 5552 may be provided on the upper side of the applicator 5520 to facilitate handling of the applicator 5520 due to the flexibility of the layer 5550. The applicator 5520 preferably comprises an attachment point for the bridge 5502 at the distal end 5505, for example using a section of double-sided adhesive tape 5528. The double-sided adhesive tape 5528 may be protected by an additional protective release layer, which is removed prior to adhering the bridge 5502 to the applicator 5520. It will be understood that different attachment methods are also contemplated, for example heat sealing, welding, or suitable adhesives. Some embodiments may also permit the manufacture of the bridge 5502 and the applicator 5520 as a single unit that does not require separate attachment means. The applicator 5520 preferably comprises at least one aperture 5526 through itself and designed to be placed over a wound site, and which can serve to fluidically connect the wound site to the source of negative pressure and to the air leak while also serving as a conduit to draw out wound exudate from the wound site.

In use, and with reference to FIGS. 2A-B, the system 5501 may be used in a similar fashion to the other embodiments previously disclosed herein. A wound site 5530 is preferably cleaned and prepared in a suitable fashion, and a wound packing material, if necessary, placed into the wound site, followed by a drape 5531. An aperture 5535 through the drape to the wound site is then created, although some embodiments may have a pre-made aperture 5535. Subsequently, an operator may situate the applicator portion 5520 over the aperture 5535. After removing the backing layer 5529 (if present) from the adhesive layer on the underside of the applicator portion 5520, the applicator is sealed to the drape 5531, and the backing layer 5552 (if present) is also removed from the applicator portion 5520. A fluidic conduit such as a tube 5540 may then be connected to the connector 5504. The tube 5540 may also be connected to connector 5504 prior to applying the applicator to the wound site. The fluidic conduit is connected to a source of negative pressure 5534, preferably with a container suitable for containing wound exudate interposed therebetween. The application of negative pressure may then be effectuated to the wound site 5530 until the wound site progresses to a desired level of healing.

During use of the system 5501, wound exudate from the wound site 5530 is drawn by the negative pressure through the lower channel layer 5516. The air leak 5524 allows air to pass through the upper channel layer 5512 into the apertures through the distal ends of the layers 5512, 5514, 5516 and 5518. The negative pressure draws air passing through the upper channel layer into the lower channel layer 5516 back toward the source of negative pressure or pump. In some embodiments, the controlled air leak 5524 provides a constant flow of air through the system 5501, which then may be used to determine whether blockage or leakage is present. Causes of blockage can include, for example, situations where the lower channel 5516 becomes occluded with wound debris. Leakage causes can include, for example, improper sealing of the drape over the wound site, or physical damage to the system 5501 leading to excess air leaking into the system. The blockage or leakage may be determined, in certain embodiments, by measuring the speed of the pump while the pump works to maintain a constant negative pressure. Pump speed may also be measured indirectly by measuring the amount of voltage or signal sent to the pump.

Figure 3A:
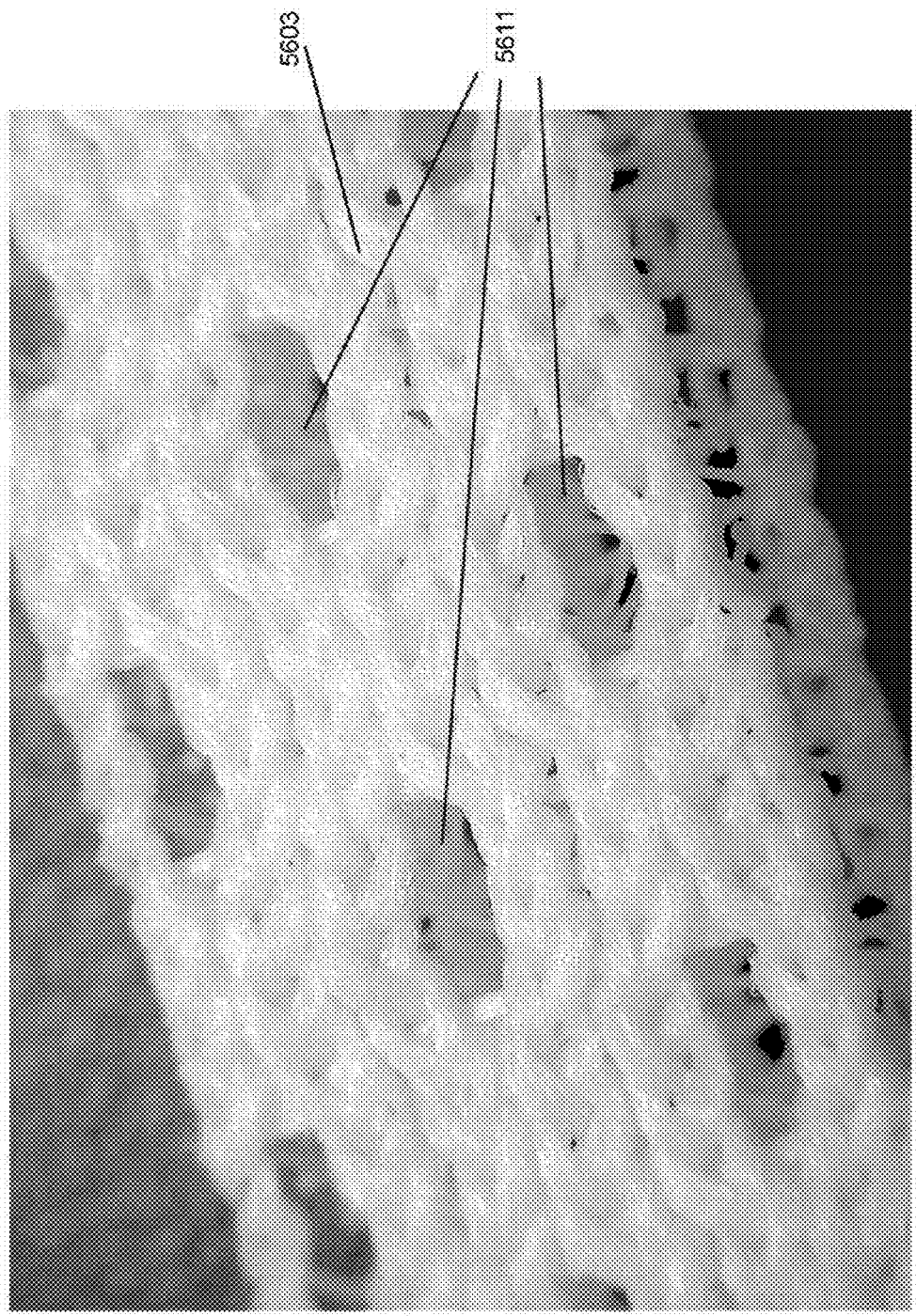
FIG. 3A illustrates a top view of a 3D fabric that may be used in a negative pressure wound treatment system.
Figure 3B:
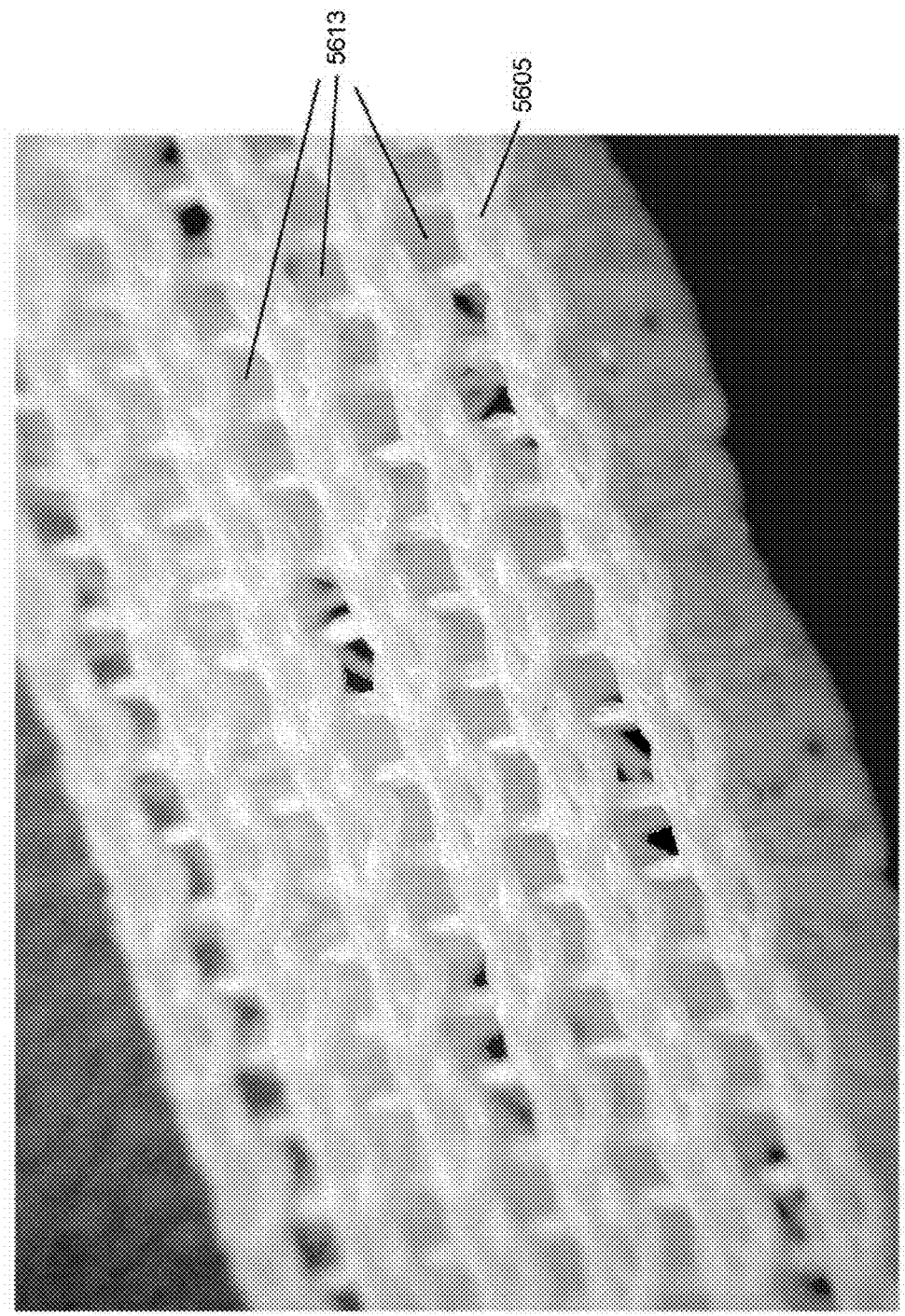
FIG. 3B illustrates a bottom view of the 3D fabric of FIG. 3A.
Figure 3C:
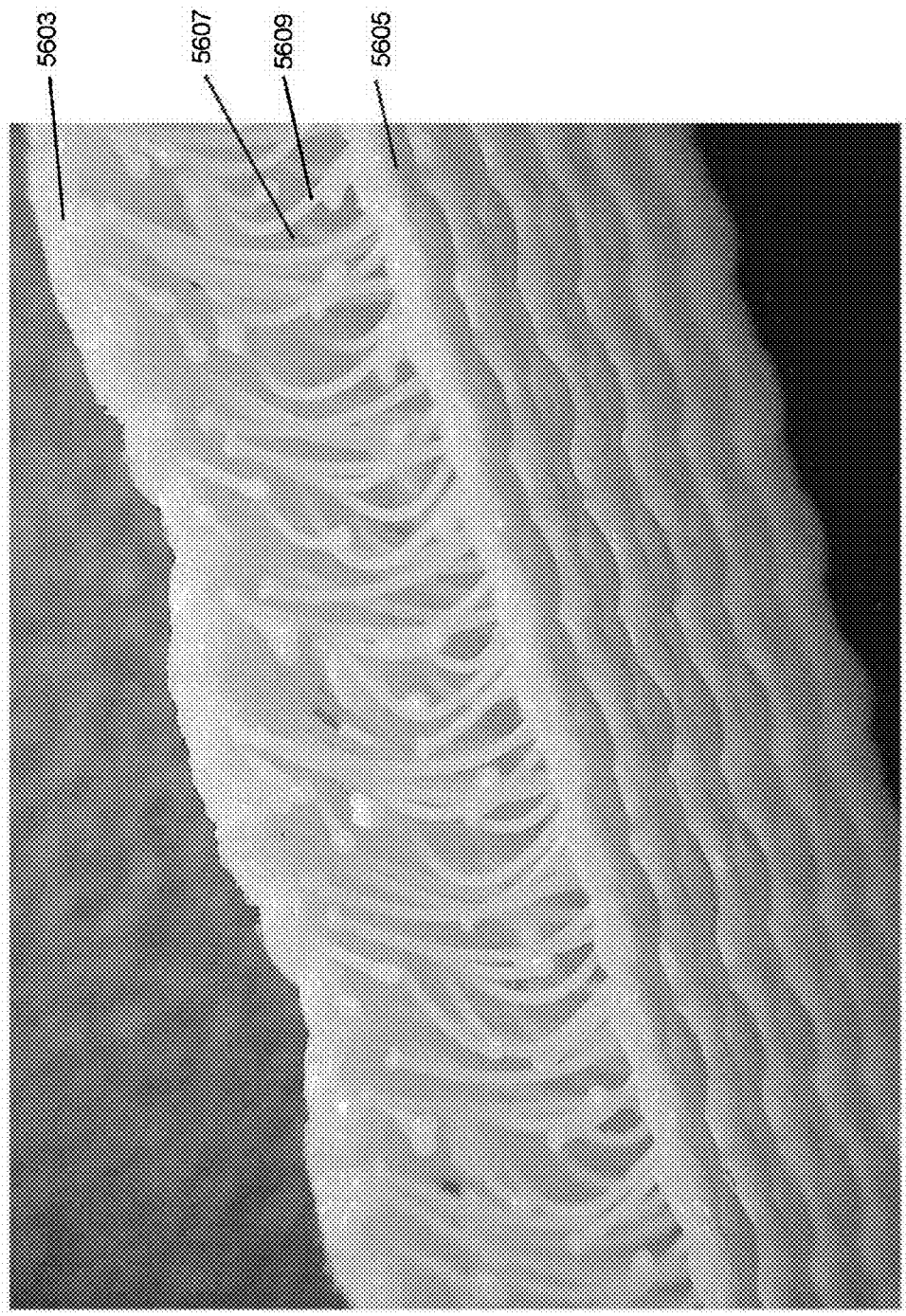
FIG. 3C illustrates a side cutaway view of the 3D fabric of FIG. 3A.

FIGS. 3A-C illustrate views of a 3D fabric that may be used in various embodiments described herein, for example the bridge 5502 of the suction adapter illustrated in FIGS. 2A-J. Although other porous materials such as foam may be used in the embodiments described herein, for example in the upper and lower channels 5512 and/or 5516 illustrated in FIGS. 2A-C, the use of 3D fabrics may be advantageous in some circumstances. Certain 3D fabrics have been found to perform well in conveying negative pressure to and wound exudate from a fluidic suction adapter, even while under compression—for example when a patient's weight is placed directly upon the suction adapter, or when negative pressure is applied—and/or when the fluidic suction adapter is kinked or folded. Some 3D fabrics that have been found to perform acceptably include knitted polyester 3D fabric, Baltex 7970®, Gehring 879®, or Coolmax®. Of course, other fibers and fabric types may be used in part or in whole to make 3D fabrics, and include without limitation polyamides such as nylon, viscose, cotton, as well as other synthetic microfibers. 3D fabrics may also be constructed at least in part from fibers such as Nomex® and Kevlar®. Other types of fabrics and materials disclosed elsewhere herein may also be used.

In one embodiment, as illustrated in FIGS. 3A-C, the 3D fabric may comprise a bottom side 5603, a top side 5605, and an open middle area 5607. FIG. 3A illustrates the bottom (wound-facing) side 5603 of a 3D fabric, which may be woven so as to create oblong or ovoid openings 5611 extending lengthwise across the fabric. In one embodiment, the oblong or ovoid openings 5611 represent or provide an open area of between 10 and 45% (or about 10% to about 45%) of the surface area of the bottom layer, more preferably 10% to 30% (or about 10% to about 30%). Here, fibers are knitted (for example by warp knitting) so as to also include these larger openings or pores that permit bulk transport of wound fluids in addition to wound fluids carried along the fibers by capillary action of the fibers. Apertures that are optionally formed in the distal end of the 3D fabric (as illustrated in FIGS. 2D and J) may also aid in the bulk evacuation of wound debris and fluids.

FIG. 3B illustrates the top side 5605 of a 3D fabric that may be used as described herein. This top side 5605 in one embodiment does not have the larger ovoid apertures 5611 of the bottom side 5603, but may have openings 5613 defined by fibers extending lengthwise and generally transversely or at an angle across the width of the fabric. As illustrated, these openings are generally rhombus-shaped. In one embodiment, these openings 5613 may represent or provide an open area greater than that of the bottom layer, for example between 30% and 50% (or about 30% and about 50%). Of course, it will be understood that the fabric presented here is a non-limiting example, and different fabric configurations and orientations are possible, for example with the top side 5605 being placed downward so as to face the wound and with the bottom side 5603 facing upward.

FIG. 3C illustrates a cross-section of a 3D fabric (the bulb-like projections on the vertical fibers in the fabric are an artifact of the cutting process). The vertically extending fibers 5609 may be woven so as to extend through the middle open area 5607 while also being connected to the bottom and top layers 5603 and 5605. Preferably, the fibers 5609 present in the open middle layer 5607 will have sufficient stiffness so as to help prevent compression of the fabric. As illustrated in this figure, and without wishing to be bound by theory, 3D fabrics that have been found to perform well will often include a larger open area 5607 in the middle portion that may permit exudates and other fluids to be effectively transported away from a wound site while under the application of negative pressure, while more densely-woven outer layers 5603, 5605 may aid in providing additional tensile strength and capillary wicking action. For example, the middle layer may include an open volume of greater than 50% (or greater than about 50%). Obviously, the resulting fabric cannot be too thick or composed of fibers that are too stiff, as the resulting suction adapter and system may not remain sufficiently flexible for comfortable usage with a patient.

It will often be advantageous to tailor the performance characteristics of the 3D fabric while in use to account for various requirements of the suction adapter. In particular, the flow rate of exudate through the fabric, for example when under compression, may be simplified by considering the porosity of the fabric. In such situations, and again without wishing to be bound by theory, the porosity of the fabric, and thus the space that will be available for fluids to travel through, may be determined in part by the knit pattern of the fibers used in creating the 3D fabric, the thickness of the fibers used therein, and their respective stiffness and hardness (especially when under compression). Fibers may also be modified by surface properties (the fibers can be flat or textured) and the number of fibers or filaments used in the resulting fabric. Compression resistance may be affected by the choice of fiber or monofilament used in the vertical axis of the fabric, and generally, a stiffer material will improve compression resistance on this axis. Other materials properties, such as hydrophobicity, may play a role. In some cases, it may be beneficial to treat the fabric to be hydrophilic, for example with a hydrophilic polymer, so as to improve wicking of fluids. Preferred embodiments of the 3D fabric used with certain suction adapters have been found to work well when Baltex® fabric is treated in such a fashion. Other possible treatments may include lipophilic coatings to prevent proteins from adhering and building up during use, which may cause clogging and loss of pressure to the wound site.

The flow rate through the 3D fabric while under the application of negative pressure may be approximated by considering each opening as a separate orifice plate subject to Bernoulli's principle while under laminar flow. To simplify calculations, the area of openings for a given area of 3D fabric may be used. Thus, the 3D fabric may be optimized to achieve a good balance between factors such as the compression resistance required and the resulting flow rate under the application of negative pressure. Further optimization will also take place with the stiffness and flow rate of the 3D fabric being tailored to application in the embodiments described herein. Optimization of the properties and dimensions of the 3D fabric will also preferably take into account a balancing between the flow rate and stiffness required and the conformability of the fabric, as a fabric that is too stiff may not bend appropriately and may also be uncomfortable on the patient. The 3D fabric should preferably be designed so as to yield when compressed against tissue, thereby preventing tissue compression (for example against bony prominences in the patient) and the discomfort and damage, such as pressure ulcers, that may follow. For example, the dimensions of the fabric may be tailored for the ultimate use of the suction adapter—smaller in the case of distal extremities such as fingers, and larger for abdominal and burn wounds. A fabric that is too stiff may also cause pressure ulcers and other such complications, although it may function acceptably in larger dimensions.

In practice, and as also described previously herein, flow rates through embodiments of the suction adapter using 3D fabrics are at least 0.08 L/min, preferably up to 10 L/min during the application of negative pressure, and should be able to handle fluid exudate drainage of at least 10 L/day. Some embodiments of the suction adapter may be configured to handle much larger wounds, including abdominal wounds, and which in some cases may exude at least 0.5 L/hr, or 12 L/day. In more extreme cases, the pump used (for example, the RENASYS EZ) may be able to evacuate up to 16 L/min, thereby evacuating a large wound to a negative pressure level of 120 mmHg in less than a minute. The pressure drop calculated due to the 3D fabric should be minimal, and the level of negative pressure measured at a wound site is preferably within 25 mmHg of the pressure level measured at the source of negative pressure. Although the pressure drop increases as the negative pressure applied increases (thus rendering the 25 mmHg target more difficult to reach), embodiments of the wound treatment system are preferably able to maintain this target pressure to at least a negative pressure of 200 mmHg. The suction adapter and system are preferably able to function within pressure ranges required for negative pressure, which are estimated to be from around 40 mmHg to 200 mmHg. Pressure ranges greater than 200 mmHg are possible, but these may in some circumstances cause patient discomfort. The apparatus may also function at lower pressure ranges, such as 20 mmHg, although at such low pressure levels the therapeutic effects resulting from negative pressure may be diminished, with the device acting more as a drainage device. Preferably, embodiments of a negative pressure treatment system are able to maintain these target pressures at the wound site within 95% of the time that negative pressure is being applied to the wound. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Preferably, the 3D fabric is able to withstand a load of at least 5.3 psi with a compression of not more than 10% of the fabric's original thickness. Further, the 3D fabric may also be able to resist compression to less than half of its original thickness when subjected to a load of 15 psi.

In a preferred embodiment, a 3D fabric may be woven from 100% polyester using yarns of 150 and 225 Denier, to yield a fabric weighing approximately 23 to 25 oz per square yard. In these cases, the fabric may be approximately 5.8-6.8 mm thick. The bottom portion of the fabric may also have several openings or pores 5611 similar to those illustrated in FIG. 3A, which may be elongated, rectangular or ovoid in shape and oriented with their long axis lengthwise along the fabric. The openings 5611 may be arranged in a plurality of rows extending lengthwise across the fabric, for example 2 to 5 rows, or more preferably 3 rows as illustrated in FIG. 3A. The openings 5611 may be spaced equidistantly from each other in each of the rows, and may form a staggered pattern from one row to another. In one embodiment, each row may have approximately 6-10 openings, more preferably 8 openings, per 2 inches (or about 50 mm). Along a given width or transverse dimension of the fabric, the transverse rows formed by the openings may have a spacing of approximately 6-10 openings, more preferably 8 openings, per 2⅛ inches (or about 54 mm). In one embodiment, the openings may have a length of between about 1/16" to about 1" lengthwise, and a width of between about 1/32" and ½ "widthwise. In one example, the openings measure approximately ⅛" (or about 3.2 mm) lengthwise and 1/32" (or about 0.79 mm) across. The 3D fabric in one embodiment may have an overall length of between about 50 and 100 mm, more preferably about 60 mm, a width between about 5 and 15 mm, more preferably about 9 mm, and a thickness of about 6 mm.

Embodiments of the systems described herein have been tested and found to perform satisfactorily. Such testing was performed by constructing suction adapters from embodiments described herein. The distal ends of the suction adapters were then placed over an aperture made onto a drape placed over a simulated wound cavity provided with a source of simulated wound fluid, which was controllable and which can vary the flow rate of the wound fluid. The simulated wound cavity was also in some cases packed with foam or some other wound packing material. In some tests, the simulated wound fluid was a 5:1 water to glycerol mix, and in others filtered horse serum (available from Oxoid, United Kingdom) was used. The proximal end of the suction adapter was then connected to a source of negative pressure, in this case a pump. Flow rate tests and other measurements were then conducted at various negative pressure ranges and simulated exudate flow rates and air leak rates.

FIGS. 4A-L illustrate embodiments of a connector 5704, similar to the connectors 1504 and 5506 described previously, and which may be used to securely connect a source of negative pressure to a channel 5716 of a suction adapter such as the ones described herein. For example, this channel 5716 may be the channels 5512 and 5516 in FIGS. 2-3. Generally, such connectors 5704 may be useful in providing a more secure connection from the source of negative pressure to a negative pressure treatment system. The use of these connectors 5704 is optional, and may not be necessary in all embodiments described herein. In use, a tube 5740 connected to the connector 5704 may pull, or other external forces may somehow disengage the connector 5704 away from the channel 5716 to which it is attached. In such situations, application of negative pressure to the wound may be reduced or stopped. Further means to secure the connector 5704 to the remainder of the system may, as described above, include bonding or attaching other layers of the treatment system, if present, to the connector 5704. For example, this may include bonding at least one of the layers 1510, 1514, 1518 to the connector 5704. The connectors 5704 may be designed so as to create a secure connection with a fabric or material used in a channel; when 3D fabrics or 3D knitted materials are used, some embodiments of the connector 5704 are configured to engage with or attach to a portion of the material or fibers of the material to create a more secure connection. Preferably, embodiments of the connector 5704 are able to withstand a pulling force of up to 20 kg before disconnection and/or failure of the connector occurs, preferably such that the connector disengages from the channel it is connected to. It will be understood that other embodiments may be configured to withstand a lower pulling force, and may be tailored to release so to prevent injury to a patient (for example, constriction of the suction adapter and/or drainage tubes around a limb).

FIGS. 4A-B illustrate an embodiment of the connector 5704a comprising two or more projections 5752 extending distally lengthwise from the preferably cylindrical main body of the connector 5704a. The main body also comprises a central channel 5755 extending lengthwise through the main body of the connector 5704a. The projections 5752 may additionally comprise one or more barbs 5754 attached thereto. Preferably, these barbs 5754 are angled proximally so as to act as anchors when pushed or inserted into the channel 5716. In some embodiments, the barbs 5754 may form an angle of 60° with the projection 5752. When the channel 5716 is a 3D fabric or knitted material, the barbs 5754 are configured to engage to the fibers therein, creating a more secure connection. At the proximal end of the connector 5704a, a lip 5756, which may be provided in a frustoconical form, may also be provided for connection to a tube 5740. The tube 5740 may be connected to the connector 5704a (as well as the other connectors described herein) for example by press-fitting, although other connections means are possible. The tube 5740 may be the same as tube 5507 in FIG. 2J, or it may be any other tube used to provide fluid communication with a source of negative pressure.

In FIGS. 4C-D, a connector 5704*b* has a proximal portion configured to fit around the exterior portion of a tube 5740, whereby the proximal portion is approximately cylindrical and has a cylindrical opening configured to receive the tube 5740, which can be secured by a press-fit. At about the center of the connector 5704*b*, a distally extending barb 5744 can be provided to attach to the channel 5716. Channels 5745 are preferably molded around the centrally-located barb 5744 and through the body of the connector 5704*b* so as to permit the flow of fluid through the connector 5704*b* and into the tube 5740.

Figure 4F:
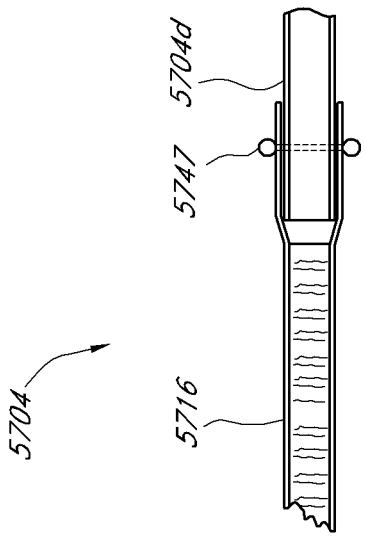
FIG. 4F illustrates an embodiment of a connector with a securing pin.
Figure 4E:
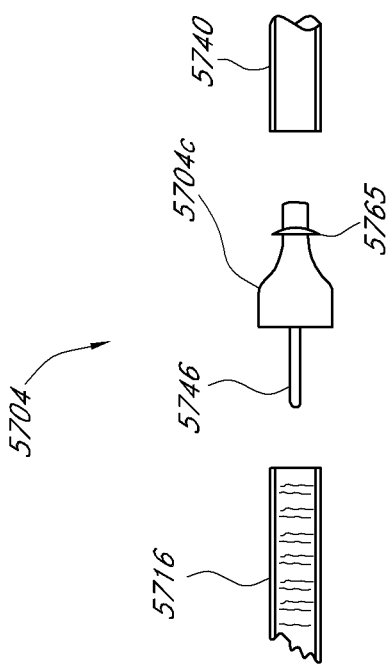
FIG. 4E illustrates an embodiment of a connector with a central rod.

FIG. 4E illustrates another embodiment of a connector 5704*c*, wherein the connector 5704*c* comprises a central, distally extending rod 5746 configured to be pushed into an inner region of the channel 5716. The connector 5704*c* is approximately cylindrical at its distal end, and tapers to form a smaller cylinder at its proximal end. It is at least partially hollowed out and has an inner channel configured to convey fluid from the material 5716 toward the tube 5740. At its proximal end, the connector 5704*c* comprises a lip 5765 similar to the lip 5742 described below in FIG. 4H, wherein the lip 5765 is configured to aid in maintaining a connection to a tube 5740 pushed onto the proximal end of the connector 5704*c*. In some configurations, the lip may 5765 may be made from rubber.

FIG. 4F illustrates an embodiment of a connector 5704*d* comprising a pin 5747 designed to secure the channel 5716 to the connector 5704*d*. Here, the connector 5704*d* may be pushed into the channel 5716. Alternatively, the channel 5716 may split partly lengthwise, so that an outer portion of the channel 5716 surrounds the connector 5704*d* when inserted therein. The pin 5747 is then inserted through the material of the channel 5716 and through apertures (not illustrated) in the connector 5704*d*. In some embodiments, the pin 5747 may have flared ends or other securement methods to prevent the pin 5747 from being displaced.

Figure 4H:
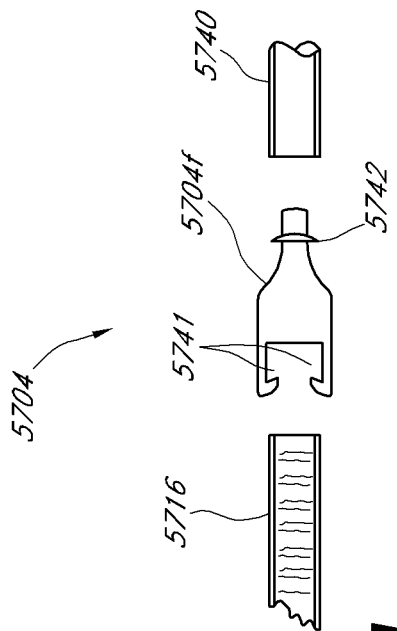
FIG. 4H illustrates an embodiment of a connector provided with hooked barbs.
Figure 4G:
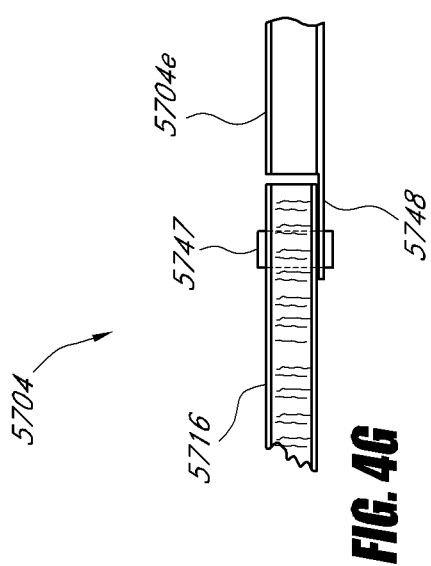
FIG. 4G illustrates a similar embodiment to FIG. 4F provided with a projection.

FIG. 4G illustrates a variation of the embodiment illustrated in FIG. 4F. Here, the connector 5704*e* may comprise a distally extending projection 5748 that extends over a portion of the channel 5716 and is configured to receive the pin 5747. In both of these embodiments, the connectors 5704*d*, 5704*e* may also be formed by creating a hole for the pin 5747 into a tube (and optionally by cutting away the tube as necessary), for example the tube 5740 illustrated previously, such that a separate connector piece is not necessary. Thus, a modified tube 5740 can replace the connector 5704*d*.

In FIG. 4H, the connector 5704*f* comprises distally extending hooked barbs 5741 that attach to upper and lower portions near the end of the channel 5716. The barbs 5741 are preferably made of an elastic or spring-like material that provides a force sufficient to sink and maintain the barbs 5741 into the material of the channel 5716. The body of the connector 5704*f* is preferably hollow so as to act as a fluid conduit. Of course, it may also be internally divided into multiple fluid channels extending through the body of the connector 5704*f*. At the other end of the connector 5704*f*, a lip 5742 may be provided to aid the connector 5704 in remaining connected to a tube 5740 so that fluids may be drained from the negative pressure treatment system.

Figure 4I:
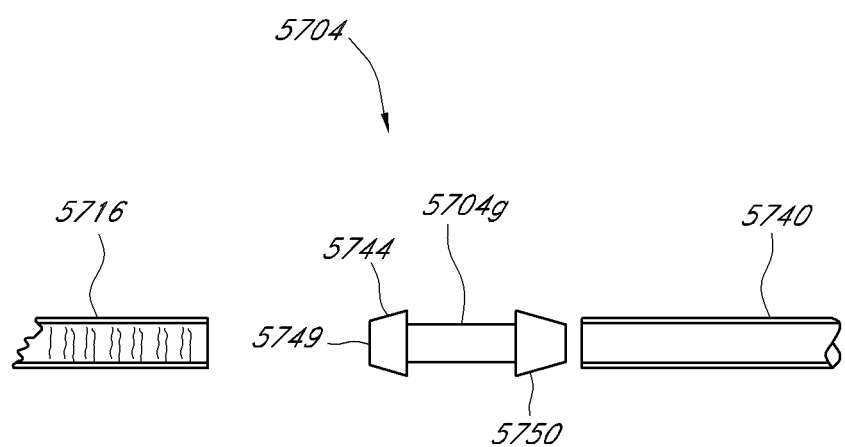
FIG. 4I illustrates an embodiment of a connector provided with a barb disposed around a central channel.

FIG. 4I illustrates an embodiment of a cylindrical hollow connector 5704*g* similar to the embodiment illustrated in FIGS. 4A-B, this time provided with a distal, frustoconical tip 5744 molded around a central channel 5749 of the connector 5704*g*. As with other embodiments, a proximal frustoconical lip 5750 may be provided so as to provide a more secure connection to a tube 5740.

Figure 4J:
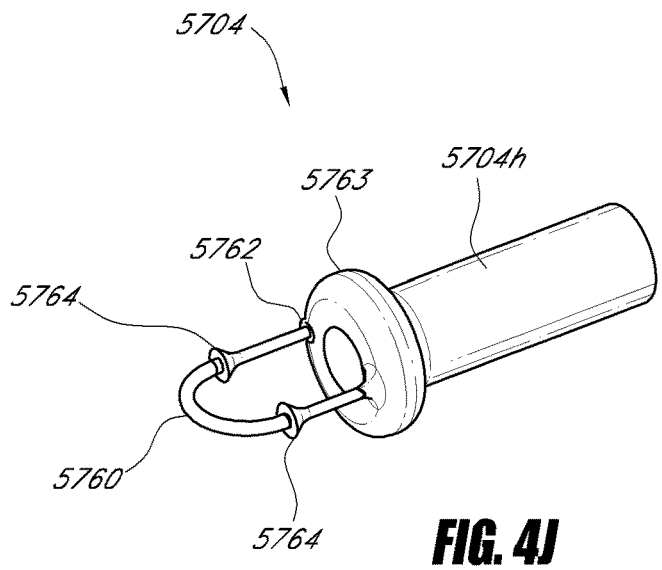
FIGS. 4J-L illustrate an embodiment of a connector comprising one or more connectors configured to be received into a corresponding cavity.
Figure 4K:
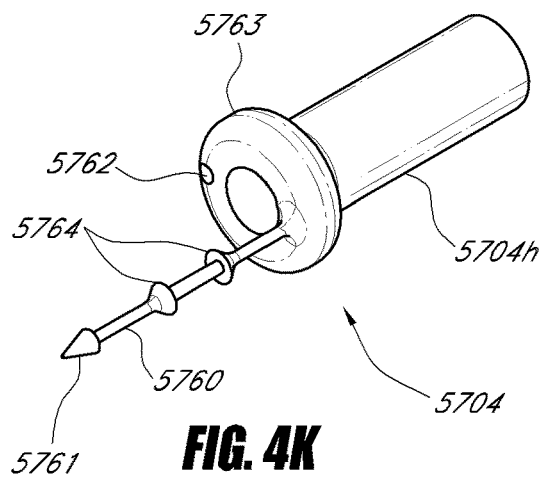
Figure 4L:
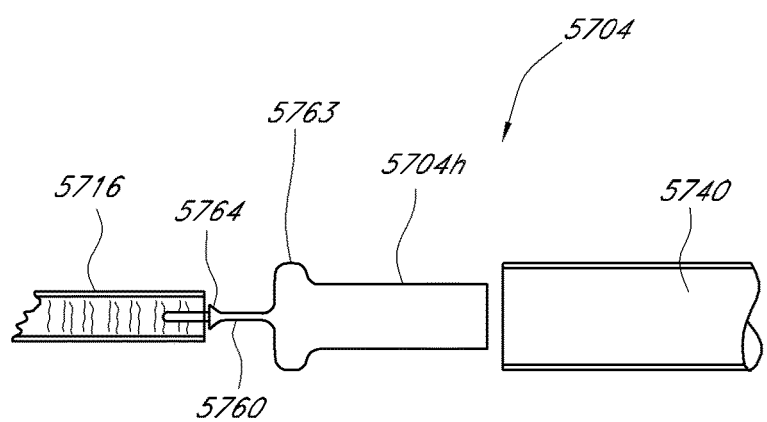
Figure 51:
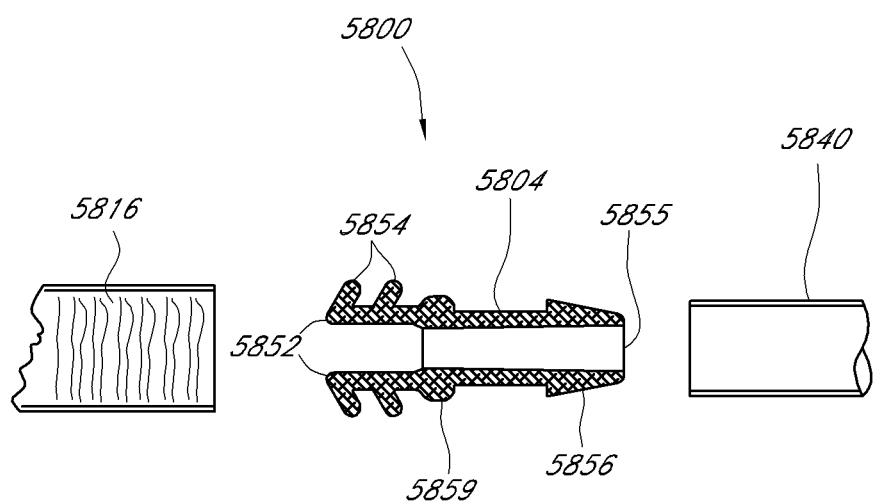

FIGS. 4J-L illustrates embodiments of a connector 5704*h* comprising a flexible line 5760 extending distally from a enlarged distal end or lip 5763 of the connector 5704*h* and forming a loop back to the enlarged distal end 5763. The line 5760 is configured to be received in a corresponding cavity 5762 formed on the enlarged distal end 5763 of the connector 5704*h*. In some embodiments, the line 5760 may have a tapered or barbed tip 5761 that is configured to securely lock into the cavity 5762. The line 5760 may also be provided with one or more barbs 5764. The body of the connector 5704*h* is preferably tubular so as to permit the flow of liquid from the wound. In use, the line 5760 may be pushed into the channel 5716 and looped around some or all of the material, followed by pushing the tip 5761 into the cavity 5762. The barbs 5764 may be useful in securing the connector 5704*h* to the channel 5716. When the channel 5716 is constructed from a 3D knitted or 3D fabric material, the line 5760 may be used to loop around and through the fibers that may extend through the middle part of the channel 5716, with the barbs 5764 helping to engage these fibers. Once secured to the channel 5716, the connector 5704*h* may be connected to a tube or other connector 5740.

FIGS. 5A-I all illustrate an embodiment of a connector 5800 similar to the connector 5704*a* illustrated in FIGS. 4A-B. In the embodiment illustrated, the connector 5800 comprises a main cylindrical body 5804, a proximal lip 5856 and distal projections 5852. A central channel 5855 extends lengthwise through the proximal lip 5856 and through the main cylindrical body. As illustrated in FIG. 5H, the central channel may have a substantially constant inner lumen at least through the proximal lip 5856 and the main cylindrical body 5804.

The distal projections 5852 may include two or more projections 5852 extending distally lengthwise from the preferably cylindrical main body 5804 of the connector 5800. These projections 5852 may additionally comprise one or more barbs 5854 attached thereto. For example, two barbs 5854 are shown on each of the projections in FIGS. 5A-I. The barbs 5854 may have sharp tips, or the tips may have rounded or blunt ends as illustrated in FIG. 5H. Preferably, these barbs 5854 are angled proximally (for example at an angle of 60° relative to the projections 5852) so as to act as anchors when pushed or inserted into the channel 5816 of a suction adapter (shown in FIG. 5I). The channel 5816 may be the same as channel 5716 of FIG. 4I or the same as channels 5512 and 5516 in FIGS. 2-3. When the channel 5816 is a 3D fabric or knitted material, the barbs 5854 are configured to engage to the fibers therein, creating a more secure connection.

The proximal portion of the projections 5852 may also comprise a reinforcing portion 5858 connecting the projections 5852 to the main body 5804, and which may be configured to provide additional strength. As illustrated in FIGS. 5B, 5C, 5G and 5H, the reinforcing portion 5858 may provide the projections 5852 with increased thickness at a proximal end of the projections 5852. This reinforcing portion 5858 may also provide additional resistance to minimize the likelihood of the projections 5852 becoming bent or twisted, for example when being inserted into the channel 5816. As illustrated in FIG. 5H, in one embodiment the distance between opposite projections 5852 may be larger than the diameter of the central channel 5855. The reinforcing portion 5858 in this embodiment serves as a transition along the inner surface of the projections 5852 to taper the opposing distance of the projections 5852 to the diameter of the central channel 5855.

In some embodiments, the distal end of the cylindrical body 5804 along its outer surface may be provided with an enlarged shoulder 5859, which is preferably rounded when viewed in profile in FIGS. 5B-E. Viewed from the bottom (as shown in FIG. 5G), part of the shoulder 5859 may be flattened to reduce its width along certain axes. If so provided, this shoulder 5859 may aid in securing the connector 5800 together with the barbs 5854 to the channel 5816. The outer diameter of the shoulder 5859 is preferably smaller than the distance between opposing barbs 5854.

At the proximal end of the connector 5800, a lip 5856, which may be provided in a frustoconical form, may also be used for connection to a tube 5840. In some embodiments, the lip 5856 may have a rounded proximal edge that may facilitate connecting to the tube 5840. As illustrated, in one embodiment the lip 5856 increases in outer dimension from its proximal end toward its distal end. At the distal end of the lip 5856, there is a step-down in outer dimension to the main cylindrical body 5804. The tube 5840 may be connected to the connector 5800 (as well as the other connectors described herein) for example by press-fitting, although other connections means are possible.

With reference to FIG. 5H, the central channel 5855 is preferably of a constant internal diameter between the proximal end of the connector 5804 and the distal end of the shoulder 5859 before the projections 5852. In some embodiments, the internal diameter of the central channel may range between 0.07-0.25 inches, for example 0.12 inches. The distance between the inner surfaces of opposing projections 5852 may typically be larger, preferably between 0.1-0.2 inches, for example 0.126 inches. The outer diameter of the main cylindrical portion 5804 of the connector 5800 preferably ranges between 0.1-0.55 inches, for example 0.19 inches. The lip 5856, as described previously, is preferably larger in diameter, and may measure between 0.2-0.3 inches, for example 0.25 inches, at its distal end or base. In some embodiments, the length of the entire connector 5800 including the projections 5852 may measure between 0.5-1 inch, for example 0.77 inches. The main body of the connector 5804, including the proximal lip 5856 and the shoulder 5859, may measure in length between 0.25 and 0.75 inches, for example 0.52 inches. The lip 5856 may measure in length between 0.1 and 0.3 inches, for example 0.2 inches. The shoulder 5859 may measure in length between 0.05 and 0.15 inches, for example 0.08 inches. The projections 5852 may measure in length between 0.15-0.3 inches, for example 0.25 inches, while the barbs 5854 may measure in length between 0.05-0.08 inches, for example 0.068 inches.

Although preferred dimensions have been provided for one embodiment of a connector 5800, it will be appreciated that connectors for use in negative pressure with other dimensions are also contemplated. This includes connectors having a length (including projections) of between 0.5 to 3 inches (between or about 0.5 to about 3 inches) and an inner diameter (of the central channel 5855) of between 0.05 to 1 inch. Suitable materials for the connector 5800 may include polymers, for example but without limitation polymers such as polypropylene, polyethylene, polystyrene, and blends thereof.

With reference again to FIG. 5I, the pulling force necessary to dislodge the connector 5800 (or any of the other connectors described herein) from the channel 5816 may be configured based on a number of factors. For example, the type and configuration of material used in the channel 5816 may be particularly selected, using materials and configurations such as described above. In addition, several features in the connector 5800 may be configured to determine how easily the connector 5800 is dislodged from the channel 5816. For example, the length and number of projections 5852, as well as the length and number of the barbs 5854 may be particularly configured. Further, the force necessary to buckle, yield or snap off the barbs 5854 also affects the pulling force necessary to dislodge the connector 5800. Additional factors, such as materials selection, post-processing of materials, adhesives, or other characteristics of the connector 5800, the channel 5816, and/or other aspects of the negative pressure treatment system may thus be tailored to modify the pulling force necessary to disconnect the connector 5800 from the channel 5816. In some embodiments, the pulling force sufficient to dislodge the connector 5800 from the channel 5816 may be tailored to fall within a range, for example, of between 1 kg to 100 kg, preferably between 10 kg to 50 kg, more preferably 20 kg or more as described above.

In some embodiments, the pulling force required to dislodge or disconnect any of the connectors described above may be optimized to provide a safety feature. For example, should an embodiment of the negative pressure treatment system 5502 become entangled or trapped while applied to a patient, the pulling force can be tailored so that a connector such as connector 5800 disconnects from the channel 5516 under such force. When the connector 5800 disconnects from the channel 5516, a separation may form between the connector and the channel layer. The layers 5514 and 5518 from the embodiment illustrated in FIG. 2D may then come together due to the negative pressure being applied to form a partial or complete seal. The resulting partial or complete blockage may be detected by a sensor and an alarm activated to alert the user to a problem with the system. In some embodiments, application of negative pressure may also be stopped upon detection of the blockage. In other embodiments the disconnection of the connector 5800 may also be sensed directly by a sensor placed adjacent the connector 5800, which may then set off an alarm. Accordingly, patient safety may be enhanced by reducing the likelihood of the system 5502 entangling a portion of a patient (e.g., a patient limb, causing a tourniquet effect) or strangling the patient.

The preceding embodiments illustrated in FIGS. 4A-L and 5A-I all share elements that make them suitable for incorporation into a flexible suction adapter system of the type described previously, and in particular for securement to a channel material such as a 3D fabric. Elements of the embodiments of connectors featuring barbs (such as FIGS. 4A-D, H, J-L; 5A-I) could be combined with other embodiments of connectors featuring pins (such as FIGS. 4F-G) to form an even more secure connection to a channel material. It will also be appreciated that the features of these connectors, particularly at the distal ends, can be incorporated onto the ends of tubes used to communicate negative pressure, such that those tubes can be directly connected to the suction adapter system.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

Many of the embodiments described above include similar components, and as such, these similar components can be interchanged in different embodiments.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A fluidic connector comprising:
    a hollow cylindrical body having a proximal end configured to be coupled to a conduit and a distal end configured to be coupled to a fluid channel comprising a fabric material;
    a central channel extending through the hollow cylindrical body; and
    two projections extending distally lengthwise from the hollow cylindrical body, each projection comprising at least one barb located thereon, wherein said at least one barb is configured to be pushed into and be retained within the fabric material of the fluid channel.

2. The fluidic connector of claim 1, wherein said at least one barb comprises an elastic or spring-like material.

3. The fluidic connector of claim 1, wherein said at least one barb is angled proximally.

4. The fluidic connector of claim 3, wherein said at least one barb extends outwardly away from the central channel.

5. The fluidic connector of claim 3, wherein said at least one barb extends inwardly toward the central channel.

6. The fluidic connector of claim 1, wherein the central channel is internally divided into a plurality of fluid channels extending through the hollow cylindrical body of the fluidic connector.

7. The fluidic connector of claim 1, further comprising at least one frustoconical lip at the proximal end of the hollow cylindrical body.

8. A fluidic connector for connecting a fluid passage tube to a fluid channel comprising a fabric material, the fluidic connector comprising:
    a hollow body comprising a central channel extending between a proximal end and a distal end of the hollow body;
    a plurality of projections extending distally from the hollow body;
    a plurality of barbs provided on each of the plurality of projections, wherein the plurality of barbs are angled proximally, the plurality of barbs being configured to be pushed into and be retained within the fabric material of the fluid channel; and
    a frustoconical lip at the proximal end of the hollow body configured to be press-fit into the fluid passage tube;
    wherein the fluidic connector is configured to withstand a pulling force of up to 20 kg before disengaging from the fluid channel.

9. The fluidic connector of claim 8, wherein the plurality of barbs extend outwardly away from the central channel.

10. The fluidic connector of claim 8, wherein the plurality of barbs extend inwardly toward the central channel.

11. The fluidic connector of claim 8, wherein the plurality of barbs are comprised of an elastic or spring-like material that provides a force sufficient to sink the plurality of barbs into the fabric material of the fluid channel and maintain the plurality of barbs within the fabric material of the fluid channel.

12. A method of creating a fluidic connection, comprising:
    providing a conduit configured to deliver negative pressure to a wound from a source of negative pressure and a suction adapter configured to deliver the negative pressure from the conduit to the wound, the suction adapter comprising an elongate fluid channel having a proximal end and a distal end and a 3D knitted or 3D fabric material extending between the proximal and distal ends; and
    fluidically coupling the conduit to the 3D knitted or 3D fabric material with a fluidic connector comprising:
        a hollow cylindrical body having a proximal end and a distal end and at least one channel extending through the body from the proximal end to the distal end, wherein the proximal end of the hollow cylindrical body is press-fit with an inner or outer surface of the conduit; and
        two projections extending distally lengthwise from the hollow cylindrical body for attaching the conduit to the 3D knitted or 3D fabric material, each projection comprising at least one barb located thereon, said at least one barb being pushed into and retained within a proximal portion of the 3D knitted or 3D fabric material.

13. The method of claim 12, wherein fluidically coupling the conduit to the 3D knitted or 3D fabric material comprises press-fitting the proximal end of the hollow cylindrical body of the fluidic connector into the conduit.

14. The method of claim 12, wherein fluidically coupling the conduit to the 3D knitted or 3D fabric material comprises pushing said at least one barb into the 3D knitted or 3D fabric material.

15. The method of claim 12, further comprising providing a source of negative pressure and fluidically coupling the conduit to the source of negative pressure.

16. The method of claim 12, further comprising providing a dressing for positioning over the wound.

17. The method of claim 16, wherein the fluidic connector is configured to transmit the negative pressure to the wound via the dressing.

* * * * *